(12) United States Patent
Mathe et al.

(10) Patent No.: US 10,004,432 B2
(45) Date of Patent: Jun. 26, 2018

(54) PIXEL RECEIVER WITH CAPACITANCE CANCELLATION FOR ULTRASONIC IMAGING APPARATUS

(71) Applicant: QUALCOMM Incorporated, San Diego, CA (US)

(72) Inventors: Lennart Karl-Axel Mathe, San Diego, CA (US); Sameer Wadhwa, San Diego, CA (US); Lingli Xia, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 344 days.

(21) Appl. No.: 14/842,826

(22) Filed: Sep. 1, 2015

(65) Prior Publication Data
US 2017/0059699 A1    Mar. 2, 2017

(51) Int. Cl.
| | |
|---|---|
| H03K 17/00 | (2006.01) |
| A61B 5/117 | (2016.01) |
| G01S 15/89 | (2006.01) |
| G06K 9/00 | (2006.01) |
| G01S 7/52 | (2006.01) |
| H03K 17/975 | (2006.01) |
| H01L 27/20 | (2006.01) |

(52) U.S. Cl.
CPC .......... *A61B 5/117* (2013.01); *G01S 7/52079* (2013.01); *G01S 15/8906* (2013.01); *G06K 9/0002* (2013.01); *H01L 27/20* (2013.01); *H03K 17/975* (2013.01)

(58) Field of Classification Search
CPC .............................. H03K 17/975; H01L 27/20
See application file for complete search history.

(56) References Cited

U.S. PATENT DOCUMENTS

| | | |
|---|---|---|
| 6,365,888 B2 | 4/2002 | Von Basse et al. |
| 8,970,537 B1 | 3/2015 | Shepelev et al. |
| 2007/0031012 A1* | 2/2007 | Sheu .................... G06K 9/0002 382/124 |

(Continued)

FOREIGN PATENT DOCUMENTS

WO    WO-2013116258 A1    8/2013

OTHER PUBLICATIONS

Sheu, Low Parasitic Capacitance and Low-Power CMOS Capacitive Fingerprint Sensor, Journal of Information Science and Engineering 26, 585-595 (2010), pp. 585-595.*

(Continued)

*Primary Examiner* — Hovhannes Baghdasaryan
(74) *Attorney, Agent, or Firm* — Loza & Loza, LLP/Qualcomm

(57) ABSTRACT

An apparatus, such as a pixel sensor for an ultrasonic imaging apparatus, is disclosed. The apparatus includes a first metallization layer coupled to a piezoelectric layer, wherein a first voltage is formed at the first metallization layer in response to an ultrasonic wave reflecting off an item-to-be-imaged (e.g., a user's fingerprint) and propagating through the piezoelectric layer, and wherein the first metallization layer is situated above a substrate; a second metallization layer situated between the first metallization layer and the substrate; and a device configured to apply a second voltage to the second metallization layer to reduce a parasitic capacitance between the first metallization layer and the substrate.

27 Claims, 12 Drawing Sheets

(56) References Cited

U.S. PATENT DOCUMENTS

2011/0215150 A1* 9/2011 Schneider ............ G06K 9/0002
235/439
2014/0352440 A1  12/2014 Fennell et al.
2014/0354596 A1  12/2014 Djordjev et al.
2014/0355376 A1  12/2014 Schneider et al.

OTHER PUBLICATIONS

Akasheh F., et al., "Development of Piezoelectric Micromachined Ultrasonic Transducers", Sensors and Actuators A: Physical, Elsevier BV, NL, vol. 111, No. 2-3, Mar. 15, 2004 (Mar. 15, 2004), pp. 275-287, XP004492127.
International Search Report and Written Opinion—PCT/US2016/047103—ISA/EPO—dated Oct. 28, 2016.
Lu Y., et al., "Ultrasonic Fingerprint Sensor Using a Piezoelectric Micromachined Ultrasonic Transducer Array Integrated With Complementary Metal Oxide Semiconductor Electronics," Applied Physics Letters, 2015, vol. 106, pp. 263503-1 to 263503-4.
Tang H., et al., "Pulse-Echo Ultrasonic Fingerprint Sensor on a Chip", 18th International Conference on Solid-State Sensor, Actuators and Microsystems (Transducers), Apr. 1, 2015 (Apr. 1, 2015), pp. 674-677, XP055309421.

* cited by examiner

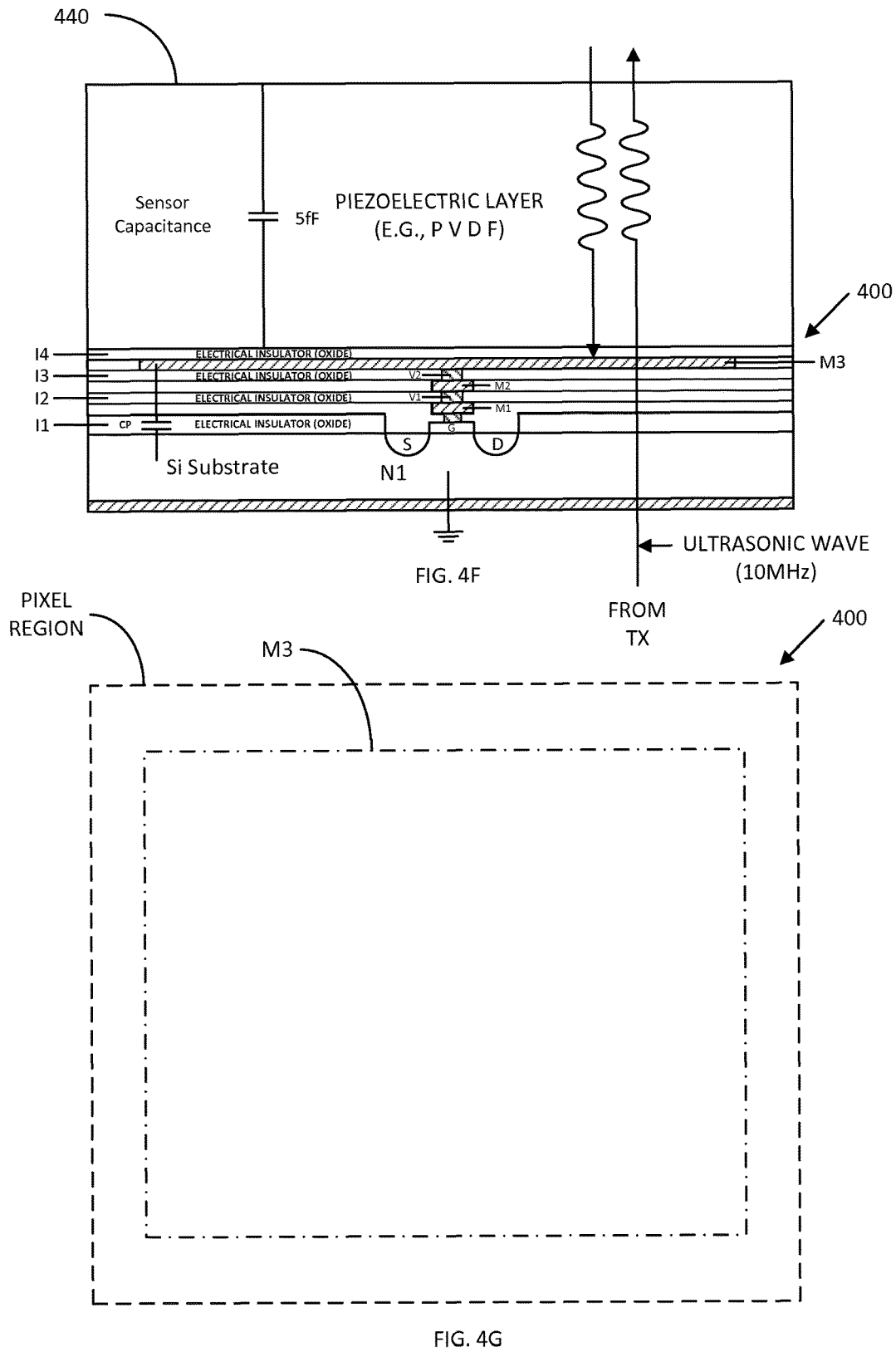

PIXEL RECEIVER WITH CAPACITANCE CANCELLATION FOR ULTRASONIC IMAGING APPARATUS

BACKGROUND

Field

Aspects of the present disclosure relate generally to ultrasonic imaging apparatuses, and more particularly, to a pixel receiver with capacitance cancellation for use in an ultrasonic imaging apparatus.

Background

An ultrasonic imaging apparatus may be used for obtaining electronic or digital images of certain items, such as fingerprints. An ultrasonic imaging apparatus typically comprises an ultrasonic wave transmitter including a transmitting piezoelectric layer (e.g., such as a polyvinylidene fluoride (PVDF) layer), a receiving piezoelectric layer (e.g., a PVDF layer), and a pixel receiver comprising a two-dimensional array of pixel sensors. Generally, the ultrasonic wave transmitter is situated below the pixel receiver, and the pixel receiver is situated below the receiving piezoelectric layer. The item-to-be-imaged, such as a user's fingerprint, is positioned above the receiving piezoelectric layer.

In operation, the transmitting piezoelectric layer of the ultrasonic wave transmitter is excited to generate an ultrasonic wave (e.g., a 10 MHz ultrasonic wave) upwards through the pixel receiver and the receiving piezoelectric layer until the wave encounters the item-to-be-imaged, such as a user's fingerprint. The ultrasonic wave reflects off the fingerprint and propagates downward towards the pixel receiver. The receiving piezoelectric layer converts the reflected wave into voltages at respective inputs of the pixel sensors of the pixel receiver. The voltages generated at the inputs of the pixel sensors are a function of whether the corresponding wave encountered a valley or ridge of the user's fingerprint.

The pixel sensors process the respective high frequency voltages to generate DC output pixel voltages. An analog-to-digital converter is provided to digitize the DC output pixel voltages. The digitized signals may then be processed by an image processor to perform various operations, such as fingerprint recognition, fingerprint database storage, and others.

In the past, the pixel receiver has been implemented using thin-film transistor (TFT) technology. However, circuits implemented using TFT technology generally have less voltage conversion efficiency and more noise than circuits implemented using other technology, such as complementary metal oxide semiconductor (CMOS) technology.

SUMMARY

The following presents a simplified summary of one or more embodiments in order to provide a basic understanding of such embodiments. This summary is not an extensive overview of all contemplated embodiments, and is intended to neither identify key or critical elements of all embodiments nor delineate the scope of any or all embodiments. Its sole purpose is to present some concepts of one or more embodiments in a simplified form as a prelude to the more detailed description that is presented later.

An aspect of the disclosure relates to an apparatus comprising a first metallization layer coupled to a piezoelectric layer, wherein a first voltage is formed at the first metallization layer in response to an ultrasonic wave reflecting off an item-to-be-imaged and propagating through the piezoelectric layer, and wherein the first metallization layer is situated above a substrate; a second metallization layer situated between the first metallization layer and the substrate; and a device configured to apply a second voltage to the second metallization layer to reduce a parasitic capacitance between the first metallization layer and the substrate.

Another aspect of the disclosure relates to a method comprising generating a first voltage at a first metallization layer in response to an ultrasonic wave reflecting off an item-to-be-imaged and propagating through a piezoelectric layer, wherein the first metallization layer is situated above a substrate; and applying a second voltage to a second metallization layer to reduce a parasitic capacitance between the first metallization layer and the substrate, wherein the second metallization layer is situated between the first metallization layer and the substrate.

Another aspect of the disclosure relates to an apparatus comprising means for generating a first voltage at a first metallization layer in response to an ultrasonic wave reflecting off an item-to-be-imaged and propagating through the piezoelectric layer, wherein the first metallization layer is situated above a substrate; and means for applying a second voltage to a second metallization layer to reduce a parasitic capacitance between the first metallization layer and the substrate, wherein the second metallization layer is situated between the first metallization layer and the substrate.

To the accomplishment of the foregoing and related ends, the one or more embodiments comprise the features hereinafter fully described and particularly pointed out in the claims. The following description and the annexed drawings set forth in detail certain illustrative aspects of the one or more embodiments. These aspects are indicative, however, of but a few of the various ways in which the principles of various embodiments may be employed and the description embodiments are intended to include all such aspects and their equivalents.

BRIEF DESCRIPTION OF THE DRAWINGS

FIG. 4F illustrates a side cross-sectional view of a portion of the pixel sensor of FIG. 4A in accordance with another aspect of the disclosure.

FIG. 4G illustrates a top view of the pixel sensor of FIG. 4A in accordance with another aspect of the disclosure.

DETAILED DESCRIPTION

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. However, it will be apparent to those skilled in the art that these concepts may be practiced without these specific details. In some instances, well-known structures and components are shown in block diagram form in order to avoid obscuring such concepts.

Figure 1:
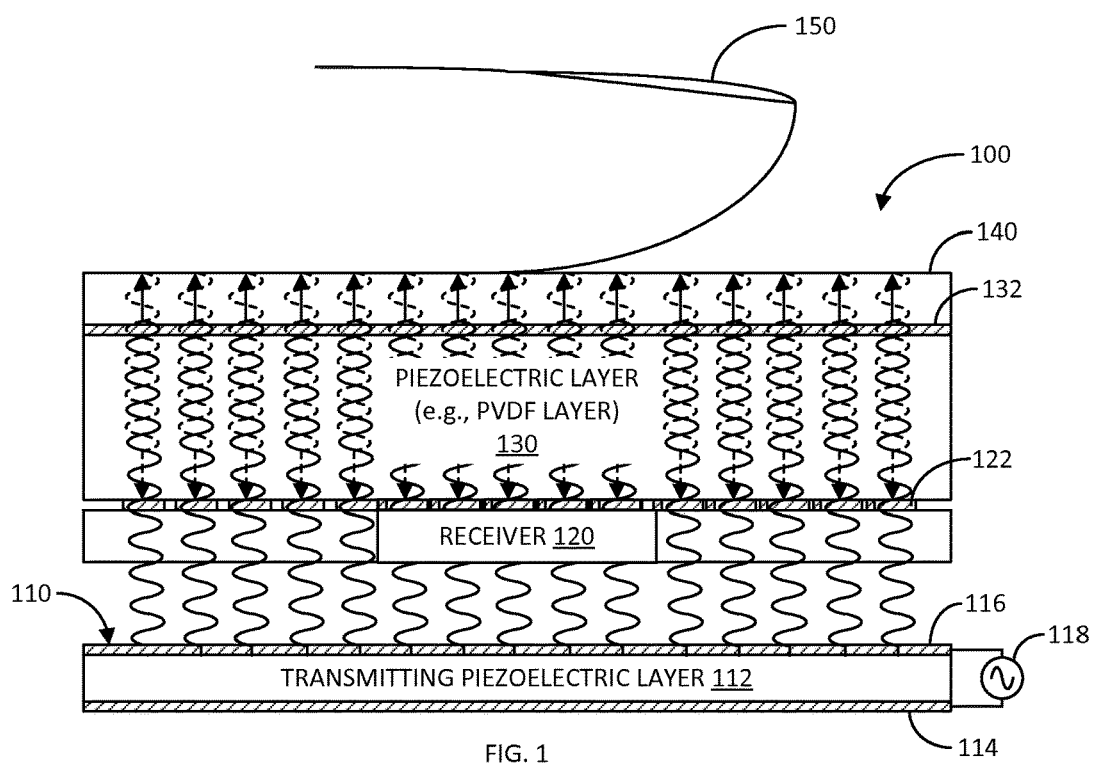
FIG. 1 illustrates a side cross-sectional view of an exemplary ultrasonic imaging apparatus in accordance with an aspect of the disclosure.

FIG. 1 illustrates a side cross-sectional view of an exemplary ultrasonic imaging apparatus 100 in accordance with an aspect of the disclosure. The ultrasonic imaging apparatus 100 comprises an ultrasonic wave transmitter 110 configured to generate an ultrasonic wave (e.g., a 10 MHz ultrasonic wave). The ultrasonic transmitter 110 is configured to generate the ultrasonic wave so that it propagates upwards through various layers, as discussed further herein.

More specifically, the ultrasonic wave transmitter 110 may comprise a transmitting piezoelectric layer 112, a pair of electrodes 114 and 116 coupled to the transmitting piezoelectric layer 112, and an excitation source 118. The piezoelectric layer 112 may comprise a polyvinylidene fluoride (PVDF) layer or other type of piezoelectric layer. The excitation source 118 is configured to generate an excitation voltage for the transmitting piezoelectric layer 112 such that layer emits an ultrasonic wave at a desired frequency (e.g., 10 MHz).

The ultrasonic imaging apparatus 100 further comprises a pixel receiver 120 positioned above the ultrasonic wave transmitter 110. A spacer (not shown), such as a glass spacer, may be sandwiched between the ultrasonic wave transmitter 110 and pixel receiver 120. As discussed further herein, the pixel receiver 120 comprises a two-dimensional array of pixel sensors configured to receive and process respective voltages associated with the item-to-be-imaged, such as a user's fingerprint. The pixel receiver 120 comprises a plurality of input metallization pads 122 arranged in a two-dimensional array for receiving input pixel voltages associated with the item-to-be-imaged.

The ultrasonic imaging apparatus 100 further comprises a receiving piezoelectric layer 130 disposed on and/or positioned above the pixel receiver 120. The receiving piezoelectric layer 130 converts the ultrasonic wave reflected off of the item-to-be-imaged (e.g., user's fingerprint) into input pixel voltages for the pixel sensors of the pixel receiver 120. Similarly, the receiving piezoelectric layer 130 may comprise a polyvinylidene fluoride (PVDF) layer or other type of piezoelectric layer. An electrode 132 (e.g., metallization layer) may be provided on top of the receiving piezoelectric layer 130 for providing a sensing window operation, as discussed further herein.

The ultrasonic imaging apparatus 100 further comprises a platen 140 disposed over the electrode 132. The platen 140 serves as a protective coating for the components of the ultrasonic imaging apparatus 100 underlying the platen. Additionally, the platen 140 serves to provide a surface upon which the item-to-be-imaged, such as a user's fingerprint 150, may be placed, as illustrated in FIG. 1.

In operation, the ultrasonic wave transmitter 110 is operated to generate a burst of ultrasonic wave (e.g., a 10 MHz ultrasonic wave) propagating upwards towards the user's finger 150 by way of the pixel receiver 120, receiving piezoelectric layer 130, and platen 140. The incident ultrasonic wave upon the user's finger 150 produces a reflected ultrasonic wave, which propagates downward through the receiving piezoelectric layer 130. The piezoelectric layer 130 converts the reflected wave into voltages at the respective inputs of the pixel sensors of the receiver 120. The amplitude of each of the voltages depends on whether the corresponding reflected ultrasonic wave portion encountered a ridge or a valley of the fingerprint. The pixel sensors process the input pixel voltages to generate output pixel voltages for further digitizing and processing in accordance with the desired imaging application.

Figure 2:
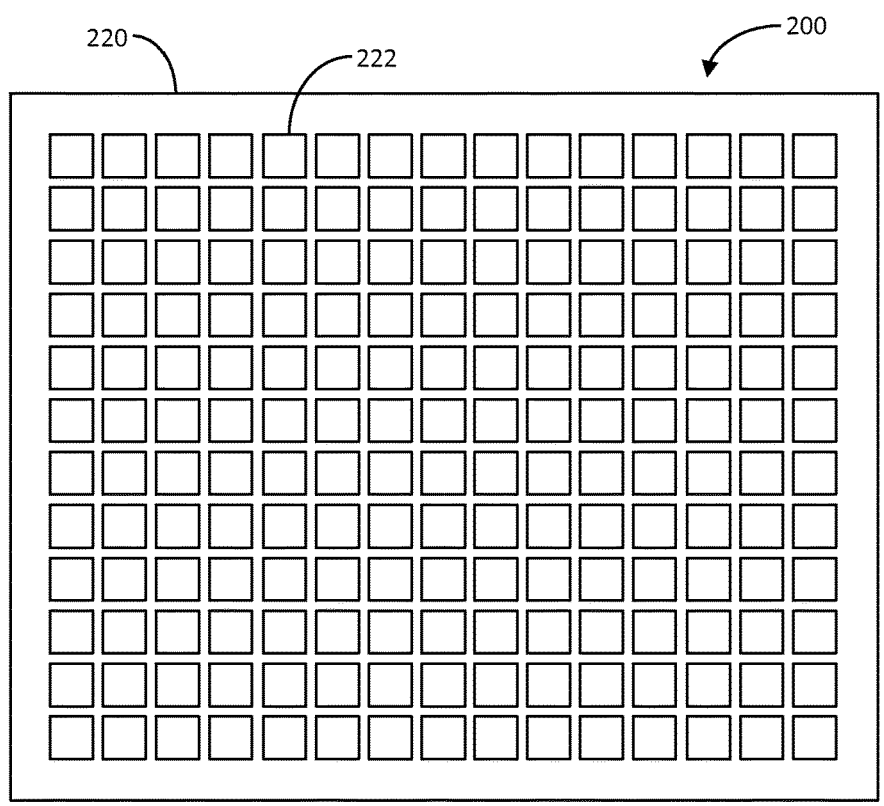
FIG. 2 illustrates a top view of an exemplary CMOS receiver for an exemplary ultrasonic imaging apparatus in accordance with another aspect of the disclosure.

FIG. 2 illustrates a top view of an exemplary CMOS receiver 200 for an exemplary ultrasonic imaging apparatus in accordance with another aspect of the disclosure. The CMOS receiver 200 may be an exemplary detailed implementation of the pixel receiver 120 of ultrasonic imaging apparatus 100 previously discussed.

The CMOS receiver 200 comprises a CMOS integrated circuit (IC) 220 including an array of pixel sensors. A top portion of the CMOS IC 220 includes a plurality of input metallization pads 222 arranged in a two-dimensional array. Although not shown in FIG. 2, the CMOS receiver 200 may include a dielectric passivation layer disposed over the array of input metallization pads 222. The receiving piezoelectric layer 130 may be attached to the top surface of the CMOS IC 220 using, for example, an adhesive material. The metallization pads 222 serve as the respective inputs to the pixel sensors of the CMOS receiver 200, where input pixel voltages related to the corresponding reflected ultrasonic wave are developed.

Figure 3:
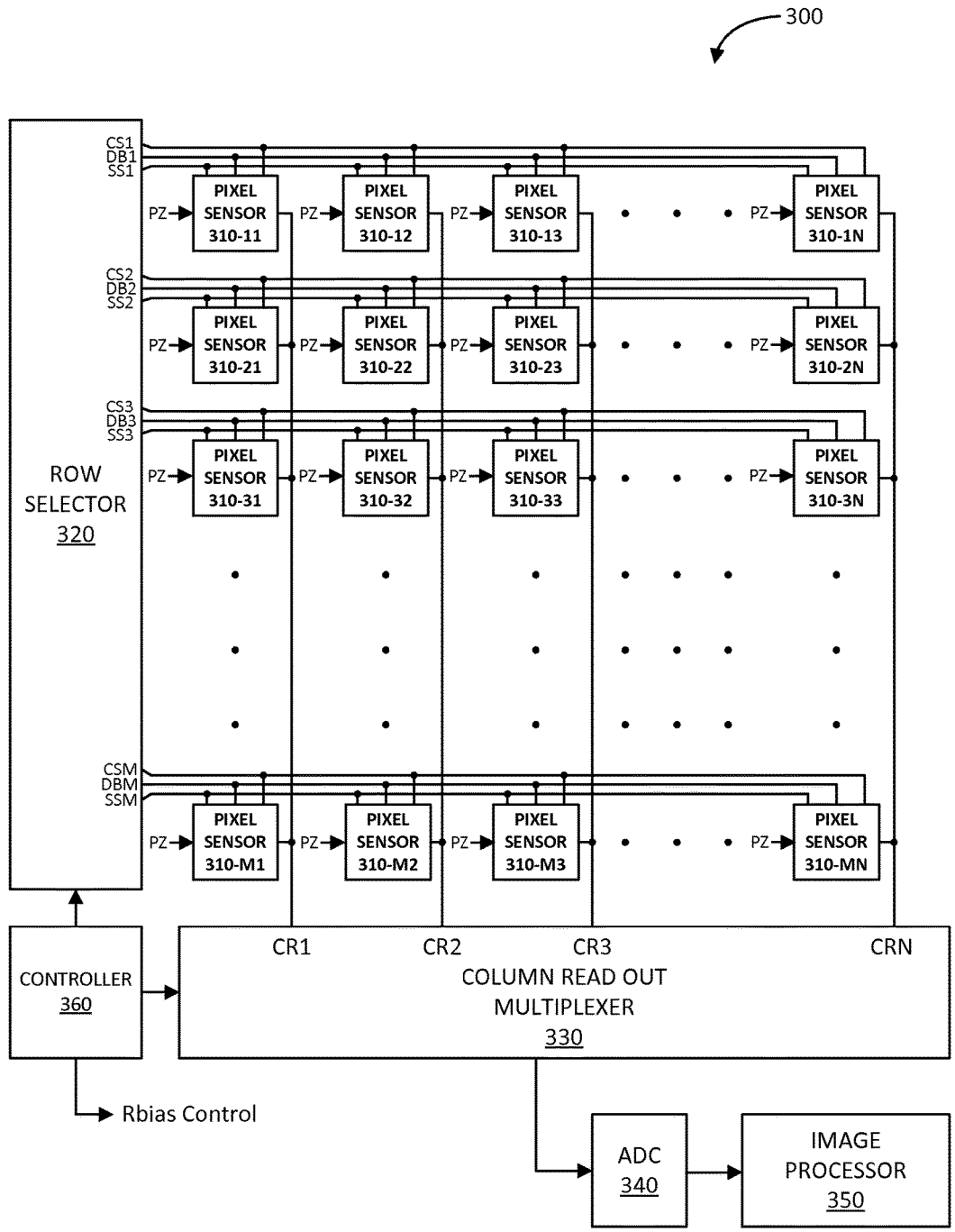
FIG. 3 illustrates a schematic diagram of an exemplary CMOS receiver for an exemplary ultrasonic imaging apparatus in accordance with another aspect of the disclosure.

FIG. 3 illustrates a schematic diagram of an exemplary CMOS receiver 300 for an exemplary ultrasonic imaging apparatus in accordance with another aspect of the disclosure. The CMOS receiver 300 may be an exemplary detailed implementation of either or both the receiver 120 and the CMOS receiver 200, previously discussed.

In particular, the CMOS receiver 300 comprises a two-dimensional array of pixel sensors 310-11 to 310-MN. In this example, the size of the pixel sensor array is M×N. That is, the pixel sensor array has M rows of pixel sensors and N columns of pixel sensors. Pixel sensors 310-11 to 310-1N are in the first row of the array; pixel sensors 310-21 to 310-2N are in the second row of the array; pixel sensors 310-31 to 310-3N are in the third row of the array; and pixel sensors 310-M1 to 310-MN are in the Mth row of the array. Similarly, pixel sensors 310-11 to 310-M1 are in the first column of the array; pixel sensors 310-12 to 310-M2 are in the second column of the array; pixel sensors 310-13 to 310-M3 are in the third column of the array; and pixel sensors 310-1N to 310-MN are in the Nth column of the array. As shown, all the of pixel sensors 310-11 to 310-MN are coupled to piezoelectric (PZ) layer for receiving respective input pixel voltages therefrom.

The CMOS receiver 300 further comprises a row selector 320, a column read out multiplexer 330, an analog-to-digital converter (ADC) 340, an image processor 350, and a controller 360. The row selector 320, under the control of the controller 360, activates a row of pixel sensors for the purposes of generating corresponding output pixel voltages. In this regard, the row selector 320 generates three signals CS1/DB1/SS1 to CSM/DBM/SSM for the rows 310-11/310-1N to 310-1M1/310-MN, respectively.

As discussed in more detail herein, the CS1 to CSM signals clear the gates of field effect transistors (FETs) in the corresponding pixel sensors of charge that may be present from a previous activation or read cycle. The DB1 to DBM signals are used to enable peak detectors in the corresponding pixel sensors for generating a voltage related to the peak energy or voltage received from the piezoelectric layer. The SS1 to SSM signals causes output pixel voltages generated by the corresponding pixel sensors to be applied to corresponding column read out lines CR1 to CRN. Also, as related to a particular embodiment, the SS1 to SSM signals are used to effectuate parasitic capacitance cancellation to increase sensitivity in the corresponding pixel sensors.

Under the control of the controller 360, the column read out multiplexer 330 reads out the output pixel voltages from the pixel sensors of the activated row. The multiplexer 330 may output the output pixel voltages in a serial manner to the ADC 340. It shall be understood that the multiplexer 330 may be configured to output at least a portion of the output pixel voltages in parallel to a plurality of ADCs, respectively. The ADC 340 digitizes the output pixel voltages and provides them to the image processor 350. The image processor 350 may perform any number of operations based on the received digitized pixel voltages. For example, the image processor 350 may perform fingerprint recognition based on a previously-stored authenticated fingerprint image.

Also, as illustrated, the controller 360 may generate an Rbias control voltage for controlling a voltage Rbias applied to the electrode, such as electrode 132, situated on a top surface of the receiving piezoelectric layer. As discussed in more detail herein, the Rbias voltage may be used to enable the peak detectors of the activated pixel sensors for detecting one or more peaks of the energy or voltage received from the piezoelectric layer.

Figure 4A:
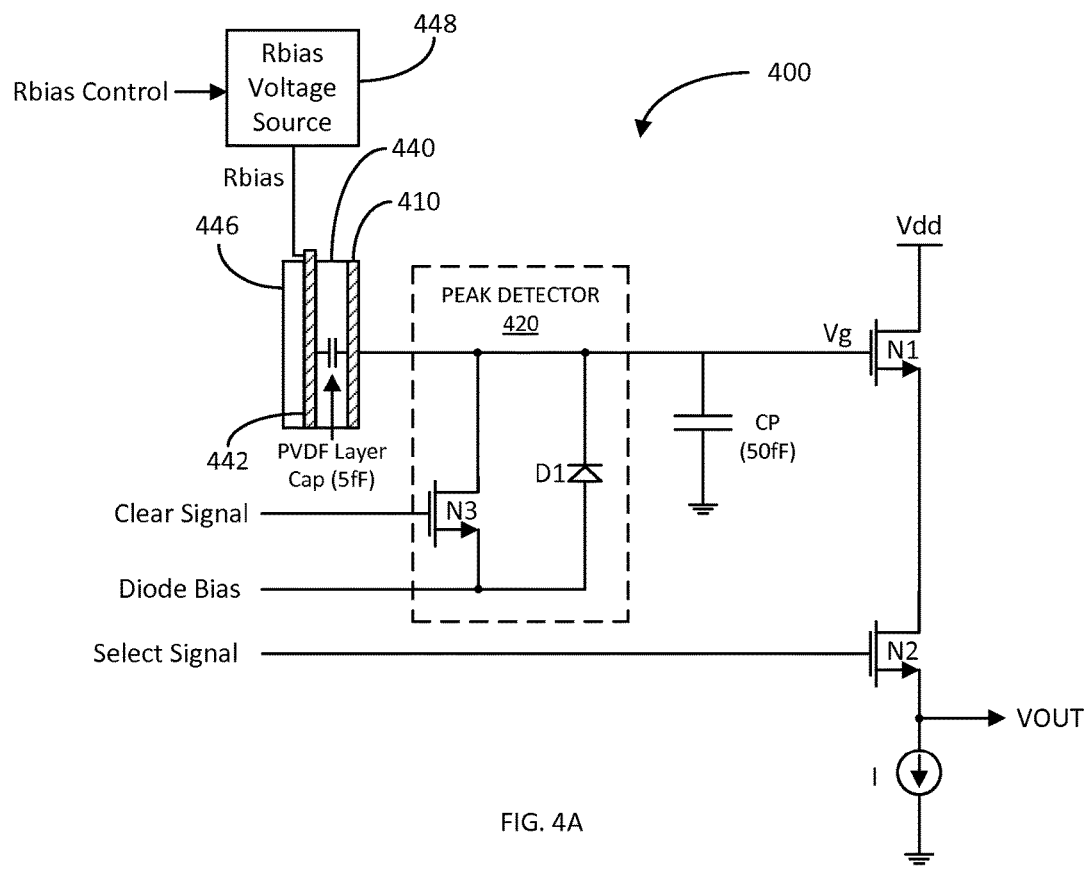
FIG. 4A illustrates a schematic diagram of an exemplary pixel sensor for an exemplary ultrasonic imaging apparatus in accordance with another aspect of the disclosure.

FIG. 4A illustrates a schematic diagram of an exemplary pixel sensor 400 for an exemplary ultrasonic imaging apparatus in accordance with another aspect of the disclosure. The pixel sensor 400 may be an exemplary detailed implementation of any of the pixel sensors 310-11 to 310-MN previously discussed. As illustrated, the pixel sensor 400 is coupled to a receiving piezoelectric layer 440, corresponding electrode 442, and platen 446, upon which an item-to-be-image, such as a fingerprint, is placed. The electrode 442 is configured to receive an Rbias voltage generated by an Rbias voltage source 448 based on an Rbias control signal generated, for example, by the controller 360 previously discussed.

In particular, the pixel sensor 400 comprises a peak detector 420 including transistor N3 and a diode D1. The transistor N3 may be configured as a field effect transistor (FET), such as an n-channel metal oxide semiconductor FET (MOSFET) (referred to hereinafter as an "NMOS."). The NMOS N3 comprises a drain coupled to an input metallization pad 410 of the pixel sensor 400, a source configured to receive a diode bias voltage, and a gate configured to receive a clear signal. The diode D1 includes an anode configured to receive the diode bias voltage and a cathode also coupled to the input metallization pad 410.

The pixel sensor 400 further comprises a source-follower amplifier comprising transistor N1. Transistor N1 may also be configured as a FET, such as an NMOS, including a drain coupled to a rail voltage (e.g., Vdd) and a gate coupled to the input metallization pad 410 of the pixel sensor 400. The pixel sensor 400 further comprises a read out transistor N2, which may also be configured as a FET, such as an NMOS, including a drain coupled to a source of the NMOS N1 and a gate configured to receive a select signal. The pixel sensor 400 further comprises a current source I coupled between the source of NMOS N2 and another rail voltage (e.g., ground).

The clear signal, diode bias, and select signal are examples of one set of the CS1/DB1/SS1 to CSM/DBM/SSM signals previously discussed. Further, the input metallization pad 410 of pixel sensor 400 is an example of one of the input metallization pads 122 and 222, previously discussed. The operation of the pixel sensor 400 is discussed below with reference to a few exemplary timing diagrams.

Figure 4B:
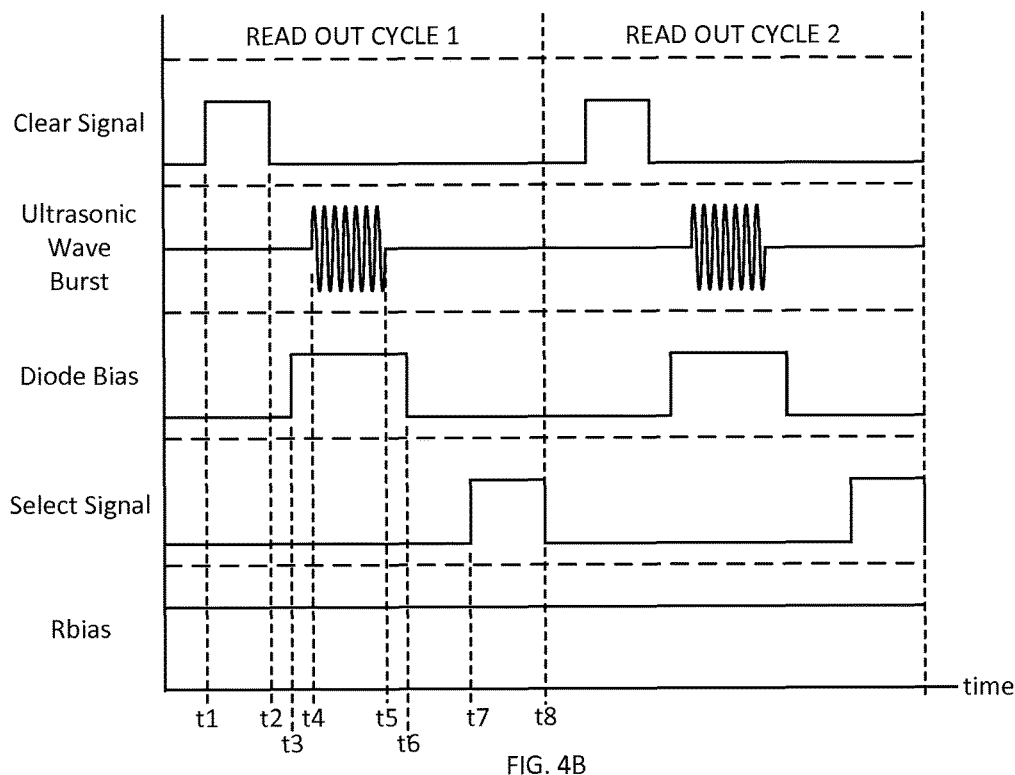
FIG. 4B illustrates a timing diagram associated with an exemplary operation of the pixel sensor of FIG. 4A in accordance with another aspect of the disclosure.

FIG. 4B illustrates a timing diagram associated with an exemplary operation of the pixel sensor 400 in accordance with another aspect of the disclosure. The horizontal or x-axis of the timing diagram represents time, the vertical axis represents the amplitudes of the clear signal, ultrasonic wave burst, diode bias, select signal, and Rbias. In the exemplary timing diagram, two consecutive read cycles 1 and 2 are shown for illustrative purposes. It shall be understood that read out cycles need not be consecutive, and may be performed at any time upon the request of a user.

According to the timing diagram, at time t1, the clear signal is first brought to an asserted state (e.g., a relatively high voltage level (e.g., Vdd)) in order to turn on NMOS N3. The turning on of NMOS N3 clears the gate of NMOS N1 of any charge that may be present, for example, from a previous read out cycle. At time t2, the clear signal is then brought to a de-asserted state (e.g., a relatively low voltage level (e.g., ground)) to turn off NMOS N3. During the time interval t1-t2, the ultrasonic transmitter may be disabled (e.g., not generating an ultrasonic wave burst), the diode bias and select signal voltages may be set to a de-asserted state (e.g., a relatively low voltage (e.g., ground)), and the Rbias may be set to any DC level (e.g., Vdd).

Then, at time t3, the diode bias voltage is brought to an asserted voltage level (e.g., 3 Volts) to bias the diode D1 for peak signal detection. The diode bias voltage may be selected on a desired operating point for the gate of NMOS N1. For example, the current source I may require about a one (1) volt across the current source; the drain-to-source voltage of NMOS N2 may require about 0.2 Volts; and the gate-to-source voltage of NMOS N1 may require 0.5 Volt. Thus, the minimum gate voltage of NMOS N1 may be 1.5 Volts. By setting the diode bias voltage to three (3) Volts, and allowing 0.7 Volt for the drop across the diode D1, the gate voltage of NMOS N1 is allowed to swing between 1.5 to 2.3 Volts. It shall be understood that the gate voltage of NMOS N1 may be set to operate within other ranges.

Then, at time t4, the ultrasonic transmitter is enabled to generate an ultrasonic wave burst through the receiving piezoelectric layer 440, electrode 442, and platen 446. As previously discussed, the ultrasonic wave bursts reflects off a user's finger and back through the piezoelectric layer 440, where an input pixel voltage (e.g., 10 MHz input voltage) is produced at the input metallization pad 410 of the pixel sensor 400. The amplitude of the input pixel voltage is a function of whether the corresponding reflected ultrasonic wave encountered a ridge or valley of the user's fingerprint.

When the input pixel voltage at the gate of NMOS N1 causes the voltage across the diode D1 to exceed the diode voltage (e.g., 0.7V), current flows through the diode D1 to charge the gate of NMOS N1. That is, considering the example where the diode bias voltage is three (3) Volts, when the input pixel voltage is at or below 2.3 Volts, current flows through the diode D1 to charge the gate of NMOS N1. Accordingly, the current that flows through the diode D1 is a function of the peak of the input pixel voltage.

Referring back to the timing diagram of FIG. 4B, after a defined time interval (t4-t5) to produce a sufficient or defined voltage Vg at the gate of NMOS N1, at time t5, the ultrasonic transmitter is disabled, and at time t6, the diode bias voltage is brought back to its de-asserted state (e.g., the relatively low voltage (e.g., ground)). During the time interval t3-t6, the clear and select signals are at their de-asserted states, and Rbias is maintained at the previous voltage level (e.g., Vdd).

After the diode bias voltage has been brought down to its de-asserted state, at time t7, the select signal is brought to its asserted state (e.g., a relatively high voltage (e.g., Vdd)) to turn on NMOS N2. This enables the source-follower amplifier comprising the NMOS N1 and the current source I. That is, the gate voltage Vg of NMOS N1, being related to the peak of the input pixel voltage received by way of the input metallization pad 410, is essentially produced as the output pixel voltage VOUT of the pixel sensor 400. More specifically, the substantially constant current I produced by the current source I through the NMOS N1 is substantially proportional to the gate-to-source voltage Vgs of the NMOS N1. Accordingly, if the gate voltage Vg of NMOS N1 increases due to the input pixel voltage and peak detection thereof, the voltage at the source of NMOS N1 likewise increases. This is why the NMOS N1 is configured as a source-follower amplifier with a gain of approximately one (1). More exact, the output pixel voltage VOUT is essentially the gate voltage Vg of NMOS N1 minus the gate-to-source voltage Vgs of NMOS N1, as NMOS N2 is fully turned on by the select signal.

As previously discussed with reference to FIG. 3, the output pixel voltage VOUT of the pixel sensor 400 is produced at a corresponding column read out line. After a defined time interval (t7-t8) sufficient for the output pixel voltage VOUT to be read out by the column read out multiplexer 330, at time t8, the select signal is brought down to its de-asserted state (e.g., a relatively low voltage (e.g., ground)) to turn off NMOS N2, and end the read out cycle 1. During the time interval t7-t8, the ultrasonic transmitter is disabled, and the clear and diode bias signals are at their de-asserted states, and Rbias is maintained at the previous voltage level (e.g., Vdd).

The following read out cycle 2 may be configured substantially the same or similar to the first read out cycle 1. Again, as previously mentioned, the following read out cycle 2 need not be performed immediately after the first read out cycle 1, but as needed, such as upon the user's request.

Figure 4C:
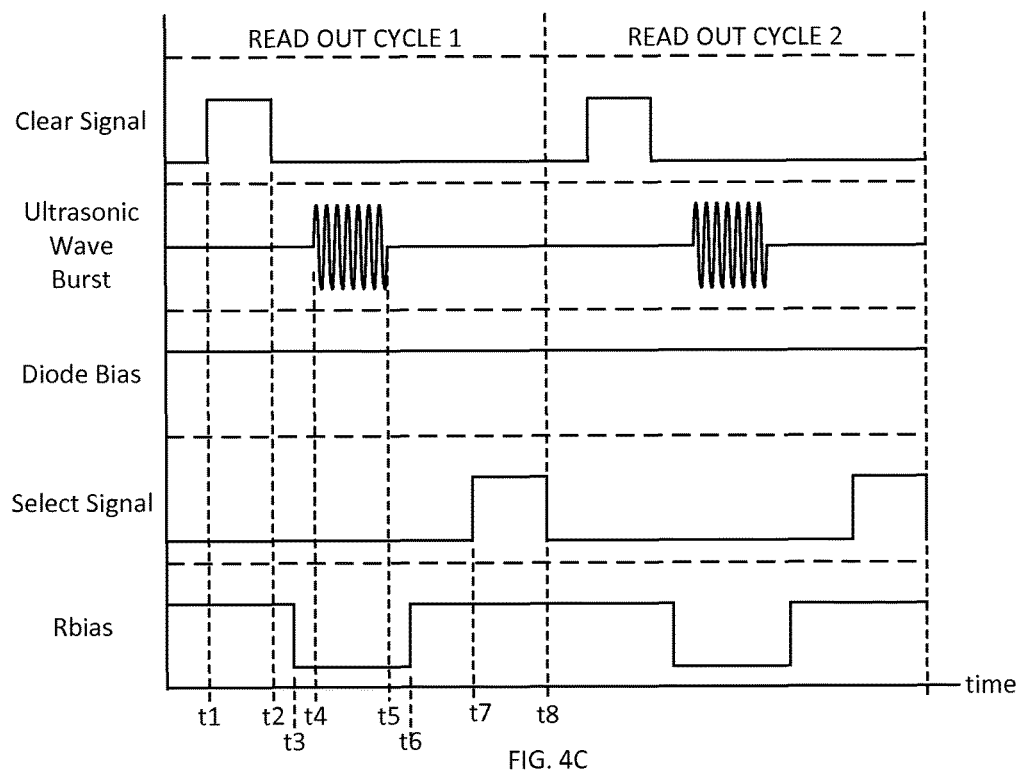
FIG. 4C illustrates a timing diagram associated with another exemplary operation of the pixel sensor of FIG. 4A in accordance with another aspect of the disclosure.

FIG. 4C illustrates another timing diagram associated with an exemplary operation of the pixel sensor 400 in accordance with another aspect of the disclosure. The operation of the pixel sensor 400 in accordance with the timing diagram of FIG. 4C is similar to that of the operation of the pixel sensor per the timing diagram of FIG. 4B, except that the Rbias signal is configured to enable and disable the peak detection circuit 420 instead of the diode bias voltage.

More specifically, with regard to read out cycle 1, at time t1, the clear signal is asserted (e.g., brought to a relatively high voltage (e.g., Vdd)) to turn on NMOS N3, and clear the gate of NMOS N1 of any charge remaining from a previous read out cycle. At time t2, the clear signal is de-asserted (e.g., brought to a relatively low voltage (e.g., ground)) to turn off NMOS N3. During the time interval t1-t2, the ultrasonic transmitter is disabled (e.g., not generating an ultrasonic wave), the select signal is de-asserted (e.g., a at relatively low voltage (e.g., ground)), and the diode bias and Rbias are at relatively high voltage levels (e.g., 3 Volts and Vdd, respectively).

At time t3, the Rbias voltage is transitioned from the relatively high voltage level (e.g., Vdd) to a relatively low voltage level (e.g., ground). Via the sensor capacitance of the receiving piezoelectric layer 440, the transition of the Rbias voltage from relatively high to relatively low causes the gate voltage of NMOS N1 to similarly transition from a relatively high voltage to a relatively low voltage. Since the diode bias voltage is maintained at a relatively high voltage level (e.g., 3 Volts), the gate voltage of NMOS N1 being brought down to the relatively low voltage enables the peak detector 420.

At time t4, the ultrasonic transmitter is enabled to generate an ultrasonic wave burst through the receiving piezoelectric layer 440, electrode 442, and platen 446. As previously discussed, the ultrasonic wave bursts reflects off of a user's finger and back through the piezoelectric layer 440, where an input pixel voltage (e.g., 10 MHz input voltage) is produced at the input metallization pad 410 of the pixel sensor 400. The amplitude of the input pixel voltage is a function of whether the corresponding reflected ultrasonic wave encountered a ridge or valley of the user's fingerprint.

When the input pixel voltage at the gate of NMOS N1 causes the voltage across the diode D1 to exceed the diode voltage (e.g., 0.7V), current flows through the diode D1 to charge the gate of NMOS N1. After a defined time interval (t4-t5) to produce a sufficient or defined voltage Vg at the gate of NMOS N1, at time t5, the ultrasonic transmitter is disabled, and at time t6, the Rbias is brought back to the previous voltage level (e.g., Vdd)). During the time interval t3-t6, the clear and select signals are at their de-asserted states, and the diode bias is maintained at the relatively high voltage level (e.g., 3 Volts).

At time t7, the select signal is brought to its asserted state (e.g., a relatively high voltage (e.g., Vdd)) to turn on NMOS N2. This enables the source-follower amplifier comprising the NMOS N1 and the current source I. Accordingly, the gate voltage Vg of NMOS N1, being related to the peak of the input pixel voltage received by way of the input metallization pad 410, is essentially produced at the output pixel voltage VOUT of the pixel sensor 400.

The output pixel voltage VOUT of the pixel sensor 400 is produced at a corresponding column read out line. After a defined time interval (t7-t8) sufficient for the output pixel voltage VOUT to be read out by the column read out multiplexer 330, at time t8, the select signal is brought down to its de-asserted state (e.g., a relatively low voltage (e.g., ground)) to turn off NMOS N2, and end the read out cycle 1. During the time interval t7-t8, the ultrasonic transmitter is disabled, the clear signal is in the de-asserted state, and the diode bias and Rbias are maintained at the relatively high voltage level (e.g., Vdd).

The following read out cycle 2 may be configured substantially the same or similar to the first read out cycle 1. Again, as previously mentioned, the following read out cycle 2 need not be performed immediately after the first read out cycle 1, but as needed, such as upon the user's request.

Figure 4D:
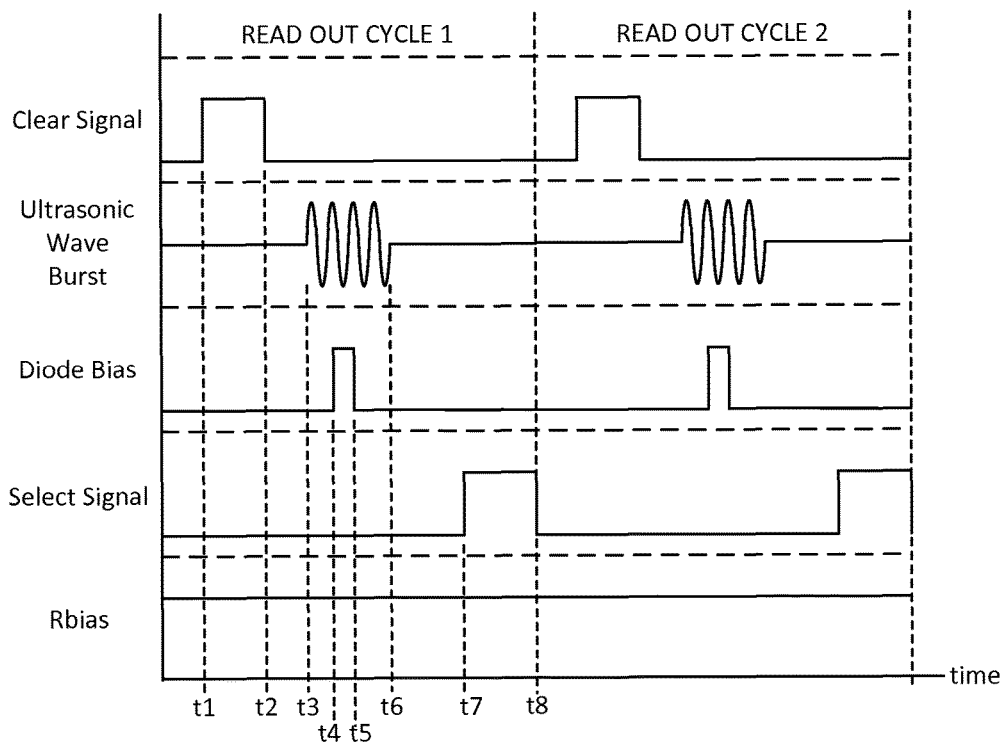
FIG. 4D illustrates a timing diagram associated with yet another exemplary operation of the pixel sensor of FIG. 4A in accordance with another aspect of the disclosure.

FIG. 4D illustrates a timing diagram associated with an exemplary operation of the pixel sensor 400 in accordance with another aspect of the disclosure. The operation of the pixel sensor 400 in accordance with the timing diagram of FIG. 4D is similar to that of the operation of the pixel sensor per the timing diagram of FIG. 4B, except that the diode bias signal is asserted for a time interval configured to detect a single negative or positive peak of the input pixel voltage.

According to the timing diagram, at time t1, the clear signal is first brought to an asserted state (e.g., a relatively high voltage level (e.g., Vdd)) in order to turn on NMOS N3. The turning on of NMOS N3 clears the gate of NMOS N1 of any charge that may be present, for example, from a previous read out cycle. At time t2, the clear signal is then brought to a de-asserted state (e.g., a relatively low voltage level (e.g., ground)) to turn off NMOS N3. During the time interval t1-t2, the ultrasonic transmitter may be disabled (e.g., not generating an ultrasonic wave burst), the diode bias and select signal voltages may be set to a de-asserted state (e.g., a relatively low voltage (e.g., ground)), and the Rbias may be set to any DC voltage level (e.g., Vdd).

Then, at time t3, the ultrasonic transmitter is enabled to generate an ultrasonic wave burst through the receiving piezoelectric layer 440, electrode 442, and platen 446. As previously discussed, the ultrasonic wave bursts reflects off of a user's finger and back through the piezoelectric layer 440, where an input pixel voltage (e.g., 10 MHz input voltage) is produced at the input metallization pad 410 of the pixel sensor 400. The amplitude of the input pixel voltage is a function of whether the corresponding reflected ultrasonic wave encountered a ridge or valley of the user's fingerprint.

During the time interval t4-t5, which may coincide with a single negative or positive peak of the ultrasonic wave burst or input pixel voltage, the diode bias is brought to a relatively high voltage level (e.g., 3 Volts) to enable the peak detector 420. With regard to detecting a single negative peak, when the input pixel voltage causes the voltage across the diode D1 to exceed the diode voltage (e.g., 0.7V), current flows through the diode D1 to charge the gate of NMOS N1. With regard to detecting a single positive peak, even though the voltage across the diode D1 may not exceed the diode voltage during a positive peak of the input pixel voltage, the non-ideal characteristic of the diode D1 still produces current through the diode based on the single positive peak to charge the gate of NMOS N1.

After the time interval (t4-t5), at time t5, the diode bias voltage is brought back to its de-asserted state (e.g., the relatively low voltage (e.g., ground)), and at time t6, the ultrasonic transmitter is disabled. During the time interval t3-t6, the clear and select signals are at their de-asserted states, and Rbias is maintained at the previous voltage level (e.g., Vdd).

After the ultrasonic transmitter is disabled, at time t7, the select signal is brought to its asserted state (e.g., a relatively high voltage (e.g., Vdd)) to turn on NMOS N2. This enables the source-follower amplifier comprising the NMOS N1 and the current source I. That is, the gate voltage Vg of NMOS N1, being related to the detected negative or positive peak of the input pixel voltage, is essentially produced as the output pixel voltage VOUT of the pixel sensor 400. The output pixel voltage VOUT of the pixel sensor 400 is produced at a corresponding column read out line.

After a defined time interval (t7-t8) sufficient for the output pixel voltage VOUT to be read out by the column read out multiplexer 330, at time t8, the select signal is brought down to its de-asserted state (e.g., a relatively low voltage (e.g., ground)) to turn off NMOS N2, and end the read out cycle 1. During the time interval t7-t8, the ultrasonic transmitter is disabled, the clear and diode bias signals are at their de-asserted states, and Rbias is maintained at the previous voltage level (e.g., Vdd).

The following read out cycle 2 may be configured substantially the same or similar to the first read out cycle 1. Again, as previously mentioned, the following read out cycle 2 need not be performed immediately after the first read out cycle 1, but as needed, such as upon the user's request.

Figure 4E:
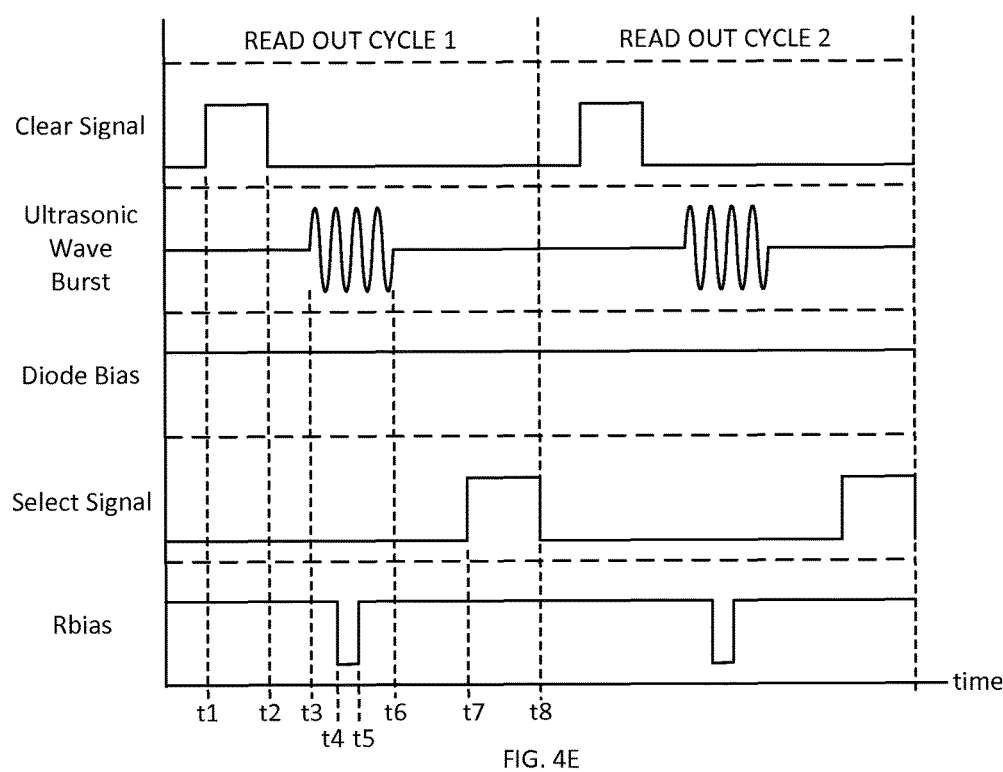
FIG. 4E illustrates a timing diagram associated with still another exemplary operation of the pixel sensor of FIG. 4A in accordance with another aspect of the disclosure.

FIG. 4E illustrates another timing diagram associated with an exemplary operation of the pixel sensor 400 in accordance with another aspect of the disclosure. The operation of the pixel sensor 400 in accordance with the timing diagram of FIG. 4E is similar to that of the operation of the pixel sensor per the timing diagram of FIG. 4D, except that the Rbias signal is configured to enable and disable the peak detection circuit 420 for a time interval of a single negative or positive peak of an input pixel voltage.

According to the timing diagram, at time t1, the clear signal is asserted (e.g., brought to a relatively high voltage (e.g., Vdd)) to turn on NMOS N3, and clear the gate of NMOS N1 of any charge remaining from a previous read out cycle. At time t2, the clear signal is de-asserted (e.g., brought to a relatively low voltage (e.g., ground)) to turn off NMOS N3. During the time interval t1-t2, the ultrasonic transmitter is disabled (e.g., not generating an ultrasonic wave), the select signal is de-asserted (e.g., at a relatively low voltage (e.g., ground), and the diode bias and Rbias are at relatively high voltage levels (e.g., 3 Volts and Vdd, respectively).

At time t3, the ultrasonic transmitter is enabled to generate an ultrasonic wave burst through the receiving piezoelectric layer 440, electrode 442, and platen 446. As previously discussed, the ultrasonic wave bursts reflects off of a user's finger and back through the piezoelectric layer 440, where an input pixel voltage (e.g., 10 MHz input voltage) is produced at the input metallization pad 410 of the pixel sensor 400. The amplitude of the input pixel voltage is a function of whether the corresponding reflected ultrasonic wave encountered a ridge or valley of the user's fingerprint.

During the time interval t4-t5, which may coincide with a single negative or positive peak of the ultrasonic wave burst or input pixel voltage, the Rbias voltage is transitioned to a relatively low voltage (e.g., ground) at time t4 and then transitioned to a relatively high voltage (e.g., Vdd) at time t5 to enable the peak detector 420 to detect a single negative or positive peak of the ultrasonic wave burst or the input pixel voltage. With regard to detecting a negative peak, when the input pixel voltage causes the voltage across the diode D1 to exceed the diode voltage (e.g., 0.7V), current flows through the diode D1 to charge the gate of NMOS N1. With regard to detecting a positive peak, even though the voltage across the diode D1 may not exceed the diode voltage during a positive peak of the input pixel voltage, the non-ideal characteristic of the diode D1 still produces current through the diode based on the detected positive peak to charge the gate of NMOS N1.

After the time interval (t4-t5), at time t6, the ultrasonic transmitter is disabled. During the time interval t3-t6, the clear and select signals are at their de-asserted states, and the diode bias is maintained at the relatively high voltage level (e.g., 3 Volts).

At time t7, the select signal is brought to its asserted state (e.g., a relatively high voltage (e.g., Vdd)) to turn on NMOS N2. This enables the source-follower amplifier comprising the NMOS N1 and the current source I. Accordingly, the gate voltage Vg of NMOS N1, being related to the peak of the input pixel voltage received by way of the input metallization pad 410, is essentially produced at the output pixel voltage VOUT of the pixel sensor 400.

The output pixel voltage VOUT of the pixel sensor 400 is produced at a column read out line. After a defined time interval (t7-t8) sufficient for the output pixel voltage VOUT to be read out by the column read out multiplexer 330, at time t8, the select signal is brought down to its de-asserted state (e.g., a relatively low voltage (e.g., ground)) to turn off NMOS N2 and end the read out cycle 1. During the time interval t7-t8, the ultrasonic transmitter is disabled, the clear signal is in the de-asserted state, and the diode bias and Rbias is maintained at the relatively high voltage level (e.g., 3V and Vdd, respectively).

The following read out cycle 2 may be configured substantially the same or similar to the first read out cycle 1. Again, as previously mentioned, the following read out cycle 2 need not be performed immediately after the first read out cycle 1, but as needed, such as upon the user's request.

FIG. 4F illustrates a side cross-sectional view of a portion of the pixel sensor 400 in accordance with another aspect of the disclosure. As illustrated, the receiving piezoelectric layer 440 is disposed on the pixel receiver including the exemplary pixel sensor 400, which, as discussed, is part of an array of pixel sensors of a CMOS receiver formed on an IC substrate (e.g., Silicon (Si) substrate). Also, as illustrated, the pixel sensor 400 comprises the NMOS N1 including a drain (D), gate (G), and source (S). As customary, the gate is formed above the substrate, and specifically, above a channel situated between the drain (D) and source (s), whereby the drain (D), channel, and source (S) are formed within the substrate.

The pixel sensor 400 further comprises a plurality of metallization layers situated above the substrate. In this example, there are three (3) metallization layers M1, M2, and M3, wherein only a relevant portion of metallization layers M1 and M2 are shown. It shall be understood that the pixel sensor 400 may be configured with any number of metallization layers. The lowest metallization layer M1 (closest to the substrate) is electrically isolated from the substrate by a first insulating layer I1 (e.g., an oxide). Similarly, the second metallization layer M2 (immediately above the first metallization layer M1) is electrically isolated from the first metallization layer M1 by a second insulating layer I2 (e.g., an oxide). In a like manner, the third metallization layer M3 (immediately above the second metallization layer M2) is electrically isolated from the second metallization layer M2 by a third insulating layer I3 (e.g., an oxide). A passivation layer I4 (e.g., an oxide) may be disposed over the top metallization layer M3 to protect the M3 layer.

The top metallization layer M3 serves as the input metallization pad 410 for the pixel sensor 400. As illustrated in FIG. 4G (top view of the pixel region), the area of the top metallization layer M3 is configured relatively large (e.g., approximately 80 percent of the entire pixel region of the pixel sensor). The reason for this is to essentially maximize the sensor capacitance between the top surface of the piezoelectric layer 440 and the top metallization layer M3. The sensor capacitance is essentially maximized to increase the input pixel voltage developed at the top metallization layer M3 in response to an ultrasonic wave reflected off a user's finger.

However, the top metallization layer M3, being made relatively large, produces a relatively large parasitic capacitance CP between the top metallization layer M3 and the substrate, which is generally grounded. As illustrated in FIG. 4A, the parasitic capacitance CP is coupled between the gate of NMOS N1 and ground. This is further illustrated in FIG. 4F, where the top metallization layer M3 is coupled to the gate of N1 by way of a metallized via hole V2, a metallized pad of the second metallization layer M2, a metallized via hole V1, a metallized pad of the first metallization layer M1, and a gate contact.

The capacitance of the parasitic capacitance CP is large compared to the sensor capacitance of the piezoelectric layer 440. For example, because of the relatively large thickness of the piezoelectric layer 440, the capacitance of the sensor capacitance may be approximately 5 femto Farads (5 fF). However, because of the relatively small thickness of the CMOS pixel sensor 400, the capacitance of the parasitic capacitance CP may be approximately 50 fF. The sensor capacitance and parasitic capacitance CP form a voltage divider that reduces the input pixel voltage generated at the top metallization layer M3 by a ratio of the sensor capacitance over the parasitic capacitance CP plus the sensor capacitance (e.g., by 5/(50+5) or 1/11). Thus, to increase the sensitivity of the pixel sensor 400, parasitic capacitance cancellation techniques are employed in the following exemplary embodiments.

Figure 5A:
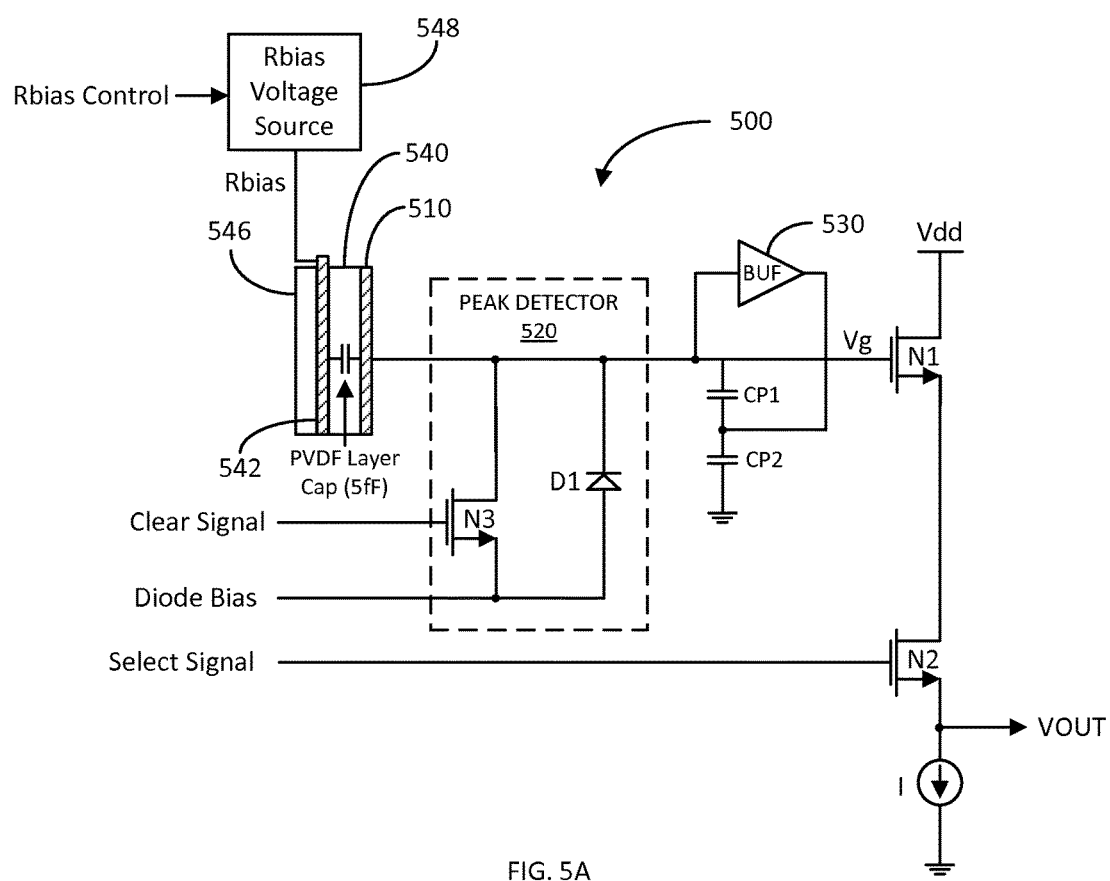
FIG. 5A illustrates a schematic diagram of another exemplary pixel sensor for an exemplary ultrasonic imaging apparatus in accordance with another aspect of the disclosure.

FIG. 5A illustrates a schematic diagram of another exemplary pixel sensor 500 for an exemplary ultrasonic imaging apparatus in accordance with another aspect of the disclosure. As previously mentioned, the pixel sensor 500 is similar to that of pixel sensor 400, except that the pixel sensor 500 further comprises elements for reducing the parasitic capacitance CP between the top metallization layer and the substrate to increase the sensitivity of the pixel sensor 500.

In particular, the pixel sensor 500 comprises an input metallization pad 510 coupled to a gate of an NMOS FET N1. A receiving piezoelectric layer 540 may be directly disposed on the input metallization pad 510 or disposed on the input metallization pad 510 by way of a passivation layer. Additionally, an electrode 542 (metallization layer) may be disposed on the piezoelectric layer 540 for providing windowing function as previously described. Further, a platen 546 may be disposed on the electrode 542, which provides a protective layer for the electrode 542 and piezoelectric layer 540. The platen 546 may also serve as a surface upon which the item-to-be-imaged, such as a user's fingerprint, may be disposed.

The pixel sensor 500 further comprises a peak detector 520 including an NMOS N3 and a diode D1. The NMOS N3 includes a drain coupled to the gate of NMOS N1, a gate configured to receive a clear signal, and a source configured to receive a diode bias voltage. The diode D1 includes an anode configured to receive the diode bias voltage and a cathode coupled to the gate of NMOS N1. The NMOS N1 includes a drain coupled to a first voltage rail (e.g., Vdd).

The pixel sensor 500 further comprises an NMOS N2 including a drain coupled to a source of NMOS N1, a gate configured to receive a select signal, and a source configured to generate an output pixel voltage VOUT for the pixel sensor 500. Additionally, the pixel sensor 500 comprises a current source I coupled between the source of NMOS N2 and a second voltage rail (e.g., ground). The NMOS N1, NMOS N2, and current source I are configured as a source-follower amplifier with a gain of approximately one (1), wherein the source-follower amplifier is enabled in response to the select signal being asserted. The pixel sensor 500 may be operated in any manner, such as those discussed with reference to timing diagrams of FIGS. 4B-4E.

As previously discussed, the pixel sensor 500 further comprises circuitry to reduce the parasitic capacitance CP between the input metallization pad 510 (e.g., the top metallization layer M3) and the grounded substrate associated with the pixel sensor. In summary, such circuitry includes an intermediate metallization layer (e.g., the second metallization layer M2) configured to act as a shield between the input metallization pad 510 and the grounded substrate. The pixel sensor 500 further comprises a buffer 530 including an input coupled to the input metallization pad 510 and an output coupled to the intermediate metallization layer.

In such configuration, two parasitic capacitances CP1 and CP2 are created; the first parasitic capacitance CP1 being coupled between the input metallization pad 510 and the intermediate metallization layer, and the second parasitic capacitance CP2 being coupled between the intermediate metallization layer and the grounded substrate. The buffer 530 is configured to apply a voltage to the intermediate metallization layer being substantially the same as the voltage at the input metallization pad 510. Accordingly, the equivalent parasitic capacitance coupled between the input metallization pad and the grounded substrate is substantially reduced since both the input metallization pad 510 and the intermediate metallization layer are at substantially the same potential or voltage. Since the second parasitic capacitance CP2 is not coupled to the input metallization pad 510, the second parasitic capacitance CP2 does not significantly affect the sensitivity of the pixel sensor 500. This capacitance cancellation technique is further described with reference to FIGS. 5B-5C.

Figure 5B:
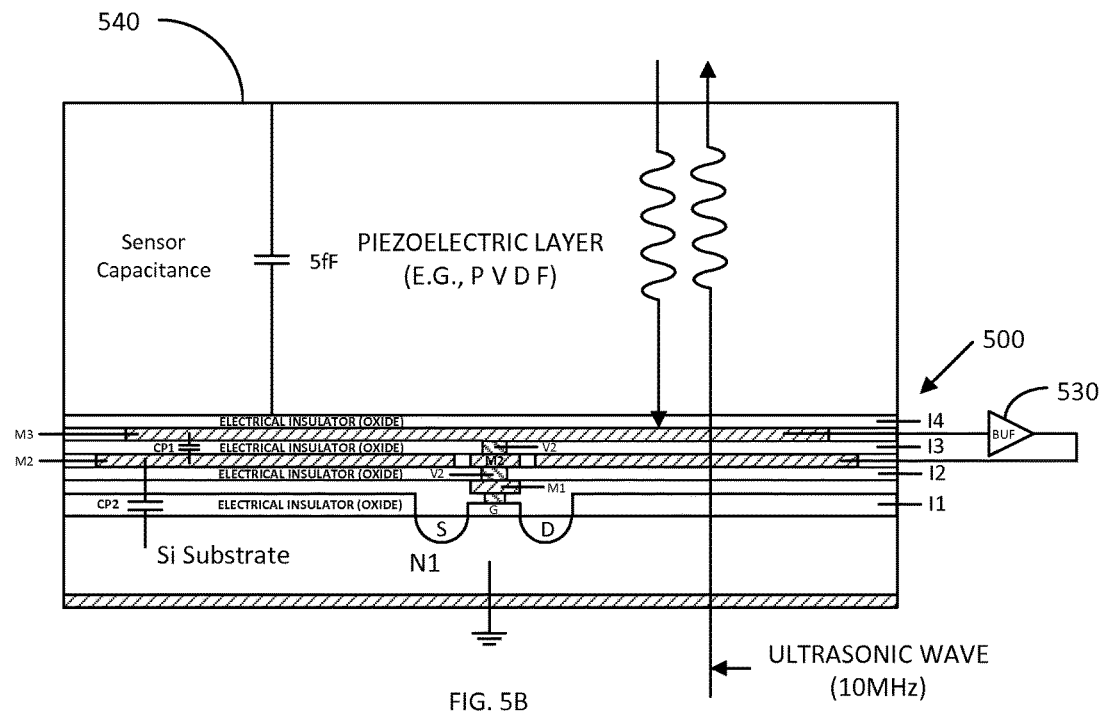
FIG. 5B illustrates a side cross-sectional view of a portion of the exemplary pixel sensor of FIG. 5A in accordance with another aspect of the disclosure.

FIG. 5B illustrates a side cross-sectional view of a portion of the exemplary pixel sensor 500 in accordance with another aspect of the disclosure. As illustrated, the piezoelectric layer 540 is disposed on a pixel receiver that includes the exemplary pixel sensor 500, which, as discussed, is part of an array of pixel sensors of a CMOS receiver formed on an IC substrate (e.g., Silicon (Si) substrate). Also, as illustrated, the pixel sensor 500 comprises the NMOS N1 including a drain (D), gate (G), and source (S). As customary, the gate is formed above the substrate, and specifically, above a channel situated between the drain (D) and source (s), whereby the drain (D), channel, and source (S) are formed within the substrate.

The pixel sensor 500 further comprises a plurality of metallization layers situated above the substrate. In this example, there are three (3) metallization layers M1, M2, and M3, wherein only a relevant portion of metallization layers M1 is shown. It shall be understood that the pixel sensor 500 may be configured with any number of metallization layers. The lowest metallization layer M1 (closest to the substrate) is electrically isolated from the substrate by a first insulating layer I1 (e.g., an oxide). Similarly, the second metallization layer M2 (immediately above the first metallization layer M1) is electrically isolated from the first metallization layer M1 by a second insulating layer I2 (e.g., an oxide). In a like manner, the third metallization layer M3 (immediately above the second metallization layer M2) is electrically isolated from the second metallization layer M2 by a third insulating layer I3 (e.g., an oxide). A passivation layer I4 (e.g., an oxide) may be disposed over the top metallization layer M3 to protect the M3 layer.

Figure 5C:
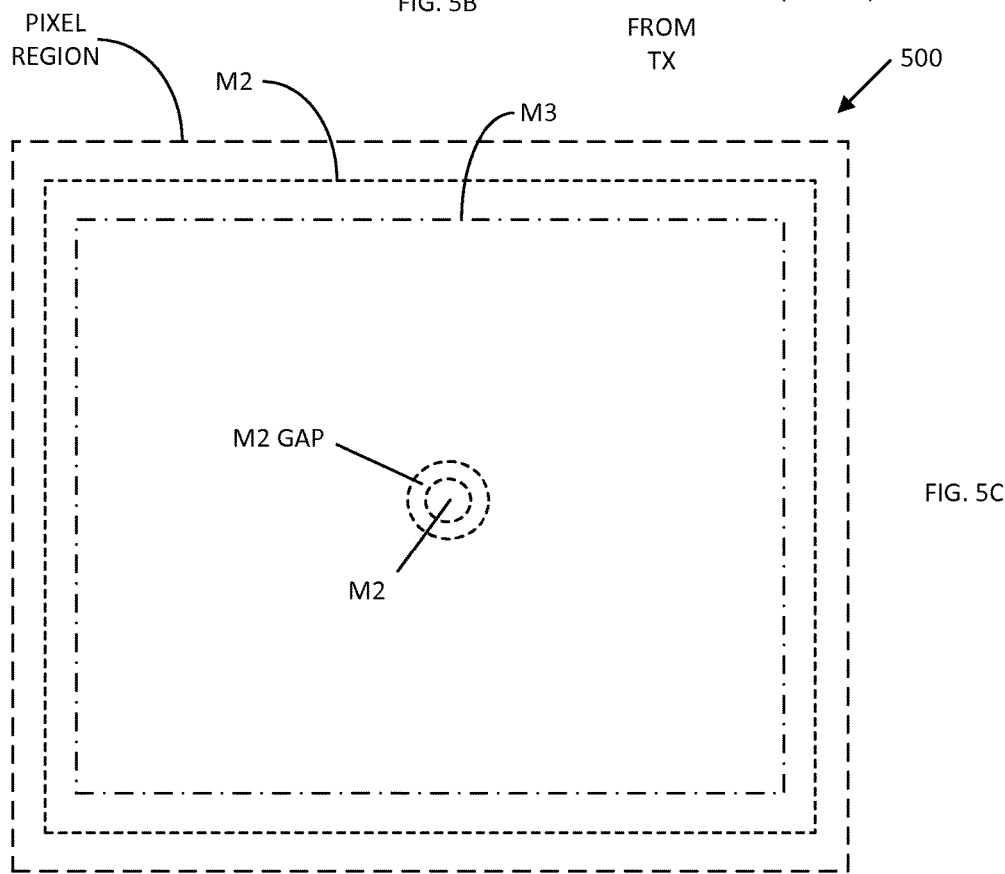
FIG. 5C illustrates a top view of the exemplary pixel sensor of FIG. 5A in accordance with another aspect of the disclosure.

The top metallization layer M3 serves as the input metallization pad 510 for the pixel sensor 500. As illustrated in FIG. 5C (top view of the pixel region), the area of the top metallization layer M3 is configured relatively large (e.g., approximately 80 percent of the entire pixel region of the pixel sensor). Again, the reason for this is to essentially maximize the sensor capacitance between the top surface of the piezoelectric layer 540 and the top metallization layer M3. The sensor capacitance is essentially maximized to increase the input pixel voltage developed at the top metallization layer M3 in response to an ultrasonic wave reflected off a user's finger.

In this exemplary embodiment, the second metallization layer M2 is configured as the shield to reduce the parasitic capacitance CP between the input metallization pad 510 (e.g., the top metallization layer M3) and the grounded substrate. As better illustrated in FIG. 5C, the area of the second metallization layer M2 is larger than the area of the top metallization layer M3. For example, the area of the second metallization layer M2 may be 90 percent of the pixel region, whereas the area of the top metallization layer M3 may be 80 percent of the pixel region. Also, as illustrated, the position of the second metallization layer M2 is such that all vertical linear paths between the top metallization layer M3 and the substrate intersect with the second metallization layer M2. This maximizes the shielding properties of the second metallization layer M2.

Also, as better illustrated in FIG. 5C, the second metallization layer M2 may include a metallized pad and a gap, wherein the metallized pad is electrically coupled to the top metallization layer M3 by way of a metallized via hole V2, and coupled to the gate of NMOS N1 by way of another metallized via hole V1, a corresponding metallized pad in the first metallization layer M1, and a gate contact. The gap is configured to electrically isolate the metallized pad of the second metallization layer M2 from the shielding portion of the second metallization layer M2. It shall be understood the second metallization layer M2 may include one or more additional pads/gaps to facilitate electrical connections through the shielding portion of the second metallization layer M2, as may be required by the pixel sensor 500.

Referring back to FIG. 5B, as previously discussed, the buffer 530 includes an input coupled to the top metallization layer M3 and an output coupled to the second metallization layer M2. Accordingly, the buffer 530 ensures that the voltage at the shielding portion of the second metallization layer M2 is substantially the same as the voltage at the top metallization layer M3. This substantially reduces the equivalent parasitic capacitance coupled between the input metallization pad and the grounded substrate. Also, as illustrated in FIG. 5B, the second parasitic capacitance CP2 between the second metallization layer M2 and the grounded substrate is not coupled to the top metallization layer M3; and hence, does not significantly reduce the input pixel voltage at the top metallization layer M3. Thus, the sensitivity of the pixel sensor 500 is improved by configuring the second metallization layer M2 as a shield through the use of the buffer 530.

Although the buffer 530 is configured to apply a voltage to the second metallization layer M2 being substantially the same as the voltage at the top metallization layer M3, it shall be understood that some capacitance cancellation may occur if the voltage applied to the second metallization layer M2 is not substantially the same, but based on the voltage at the top metallization layer M3. For example, the equivalent capacitance CP between the top metallization layer M3 and the grounded substrate may be given by the following equation:

$$CP = CP1*(1-G)$$

Where G is the buffer gain, and CP1 is the capacitance between the metallization layers M3 and M2. If buffer gain is 0.75, the capacitance CP is 25% of CP1, which is a capacitance cancellation of 75%. If buffer gain is 1, then CP is zero (0), which is a capacitance cancellation of 100%.

Figure 6A:
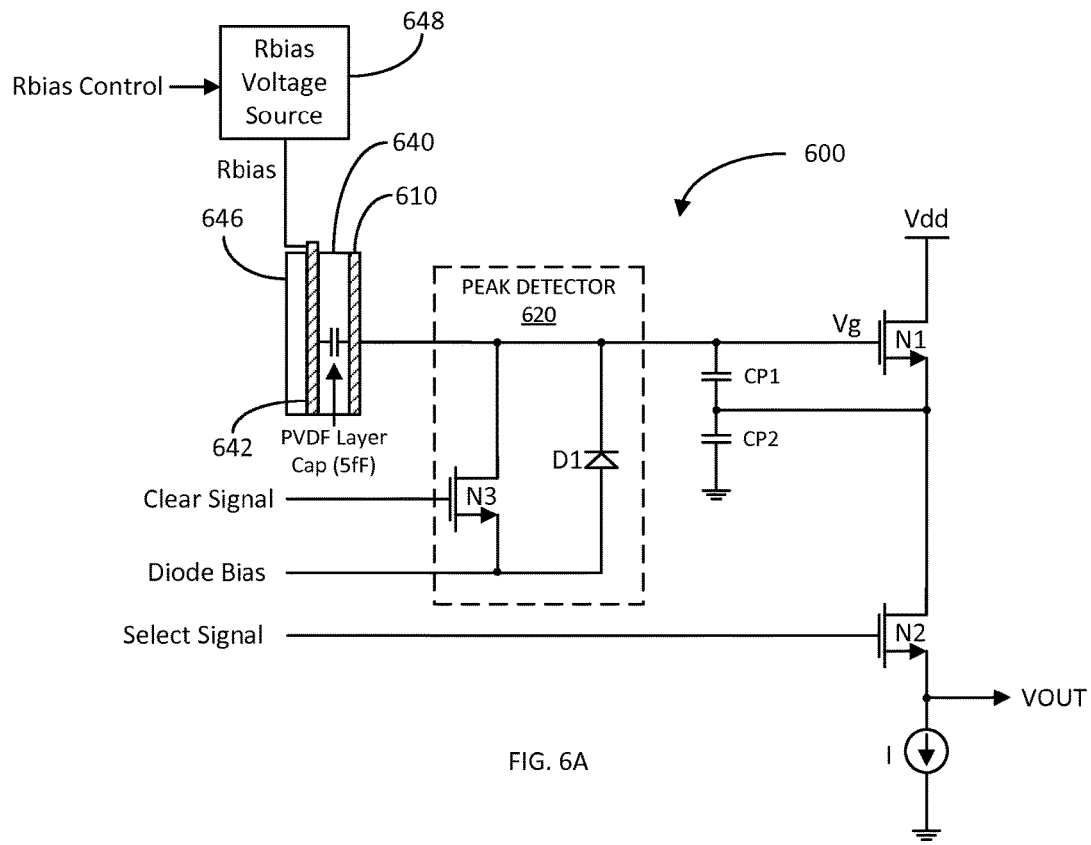
FIG. 6A illustrates a schematic diagram of another exemplary pixel sensor for an exemplary ultrasonic imaging apparatus in accordance with another aspect of the disclosure.

FIG. 6A illustrates a schematic diagram of another exemplary pixel sensor 600 for an exemplary ultrasonic imaging apparatus in accordance with another aspect of the disclosure. The pixel sensor 600 is similar to that of pixel sensor 500, except that no buffer is required to generate a voltage at the shielding metallization layer substantially the same as the voltage at the input metallization pad of the pixel sensor 600. Instead, the source of NMOS N1 is coupled to the shielding metallization layer. As previously discussed, the NMOS N1 is configured as a source-follower amplifier with a gain of substantially one (1) in read out cycle. Accordingly, the voltage at the source of NMOS N1 is substantially the same as the voltage at the gate of NMOS N1. By coupling the source of NMOS N1 to the shielding metallization layer, the voltage at the shielding metallization layer is substantially the same as the voltage at the top metallization layer. As a result, the equivalent parasitic capacitance coupled between the input metallization pad and the grounded substrate is substantially reduced.

In particular, the pixel sensor 600 comprises an input metallization pad 610 coupled to a gate of an NMOS FET N1. A receiving piezoelectric layer 640 may be directly disposed on the input metallization pad 610 or disposed on the input metallization pad 610 by way of a passivation layer. Additionally, an electrode 642 (metallization layer) may be disposed on the piezoelectric layer 640 for providing windowing function as previously described. Further, a platen 646 may be disposed on the electrode 642, which provides a protective layer for the electrode 642 and piezoelectric layer 640. The platen 646 may also serve as a surface upon which the item-to-be-imaged, such as a user's fingerprint, may be disposed.

The pixel sensor 600 further comprises a peak detector 620 including an NMOS N3 and a diode D1. The NMOS N3 includes a drain coupled to the gate of NMOS N1, a gate configured to receive a clear signal, and a source configured to receive a diode bias voltage. The diode D1 includes an anode configured to receive the diode bias voltage and a cathode coupled to the gate of NMOS N1. The NMOS N1 includes a drain coupled to a first voltage rail (e.g., Vdd).

The pixel sensor 600 further comprises an NMOS N2 including a drain coupled to a source of NMOS N1, a gate configured to receive a select signal, and a source configured to generate an output pixel voltage VOUT for the pixel sensor 600. Additionally, the pixel sensor 600 comprises a current source I coupled between the source of NMOS N2 and a second voltage rail (e.g., ground). The NMOS N1, NMOS N2, and current source I are configured as a source-follower amplifier with a gain of substantially one (1), wherein the source-follower amplifier is enabled in response to the select signal being asserted.

As previously discussed, the pixel sensor 600 further comprises circuitry to reduce the parasitic capacitance CP between the input metallization pad 610 (e.g., the top metallization layer M3) and the grounded substrate associated with the pixel sensor. In summary, such circuitry includes an intermediate metallization layer (e.g., the second metallization layer M2) configured to act as a shield between the input metallization pad 610 and the grounded substrate. The pixel sensor 600 further comprises an electrical connection coupling the source of NMOS N1 to the intermediate metallization layer.

In such configuration, two parasitic capacitances CP1 and CP2 are created; the first parasitic capacitance CP1 being coupled between the input metallization pad 610 and the intermediate metallization layer, and the second parasitic capacitance CP2 being coupled between the intermediate metallization layer and the grounded substrate. The source of NMOS N1, being coupled to the intermediate metallization layer, results in the voltage at the intermediate metallization layer being substantially the same as the voltage at the input metallization pad 610. Accordingly, the equivalent parasitic capacitance coupled between the input metallization pad and the grounded substrate is substantially reduced since both the input metallization pad 610 and the intermediate metallization layer are at substantially the same potential or voltage. Since the second parasitic capacitance CP2 is not significantly coupled to the input metallization pad 610, the second parasitic capacitance CP2 does not significantly affect the sensitivity of the pixel sensor 600. This capacitance cancellation technique is further described with reference to FIG. 6B.

Figure 6B:
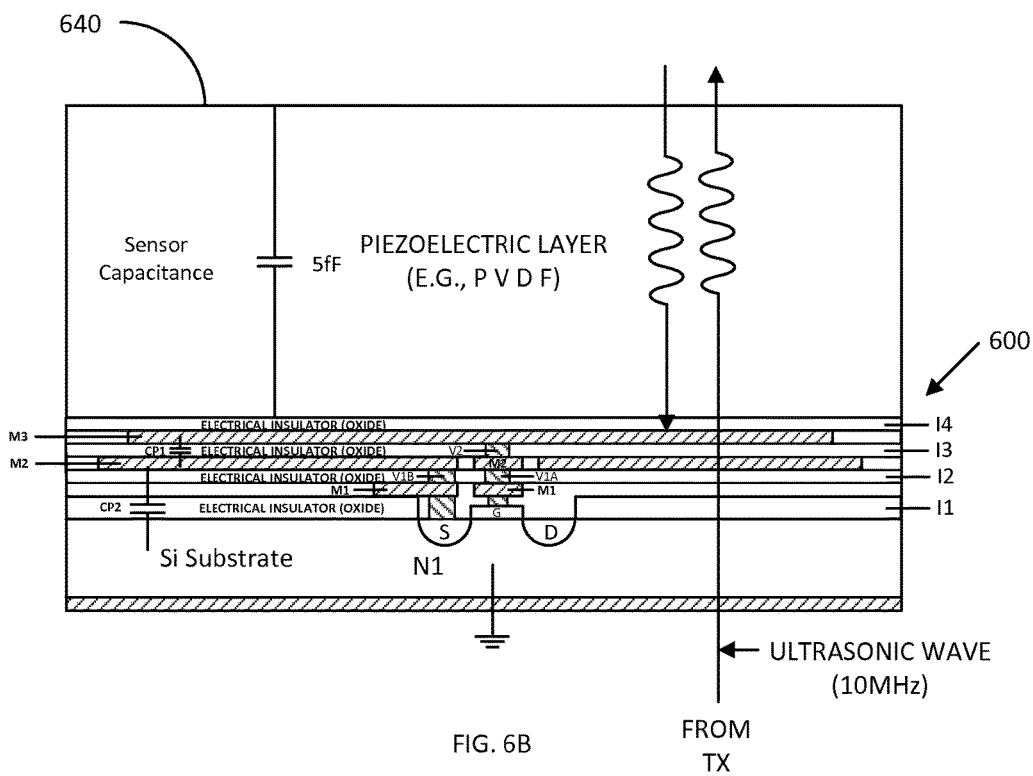
FIG. 6B illustrates a side cross-sectional view of a portion of the exemplary pixel sensor of FIG. 6A in accordance with another aspect of the disclosure.
Figure 6C:
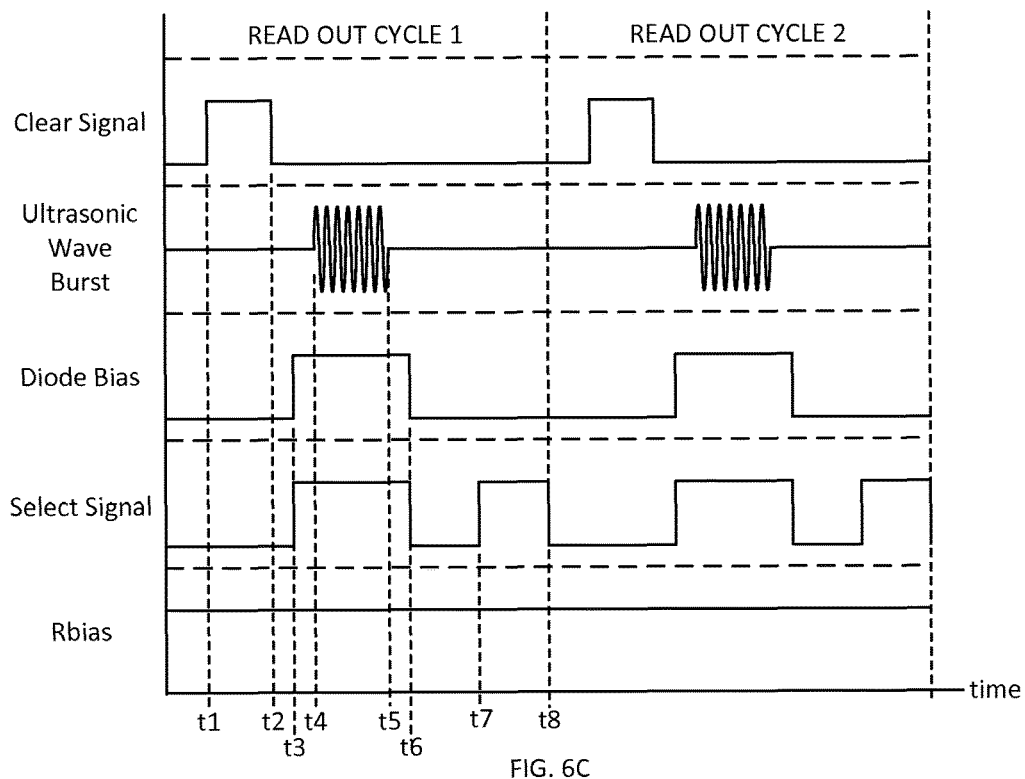
FIG. 6C illustrates a timing diagram associated with an exemplary operation of the pixel sensor of FIG. 6A in accordance with another aspect of the disclosure.
Figure 6D:
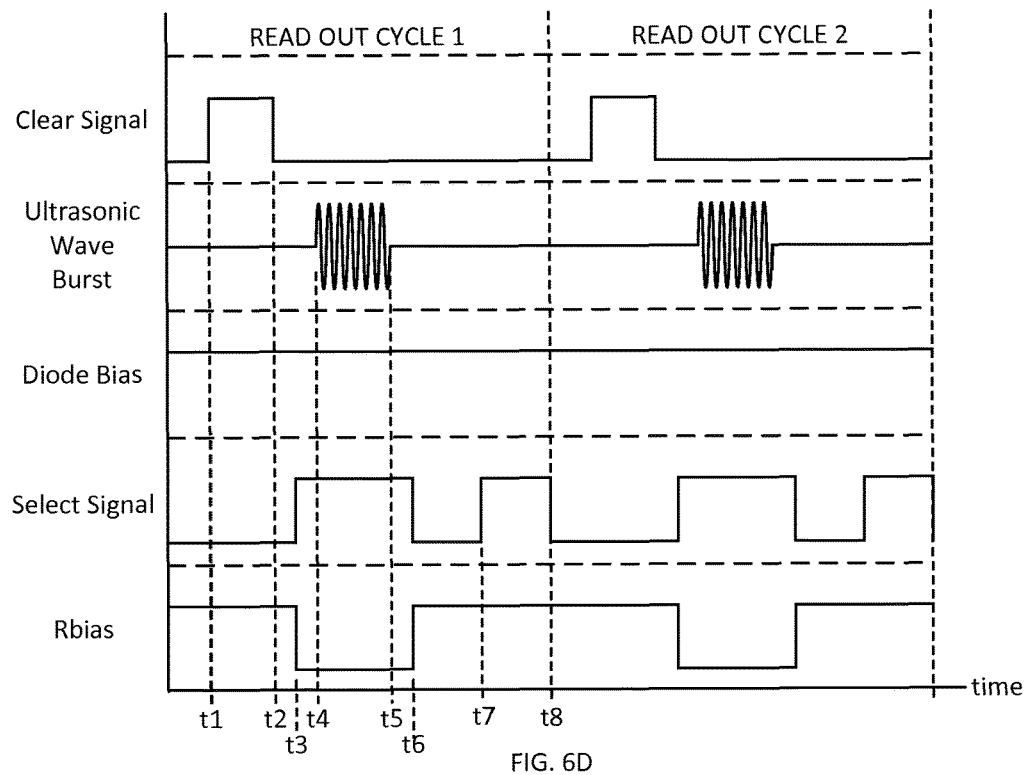
FIG. 6D illustrates a timing diagram associated with another exemplary operation of the pixel sensor of FIG. 6A in accordance with another aspect of the disclosure.
Figure 6E:
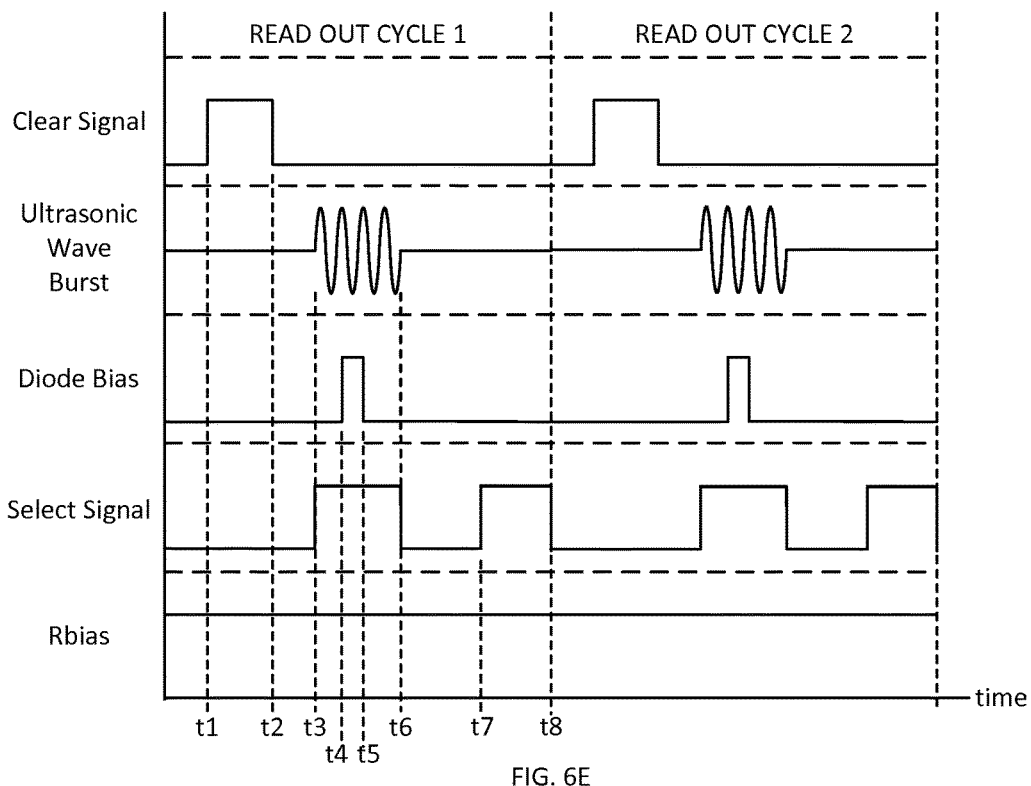
FIG. 6E illustrates a timing diagram associated with yet another exemplary operation of the pixel sensor of FIG. 6A in accordance with another aspect of the disclosure.
Figure 6F:
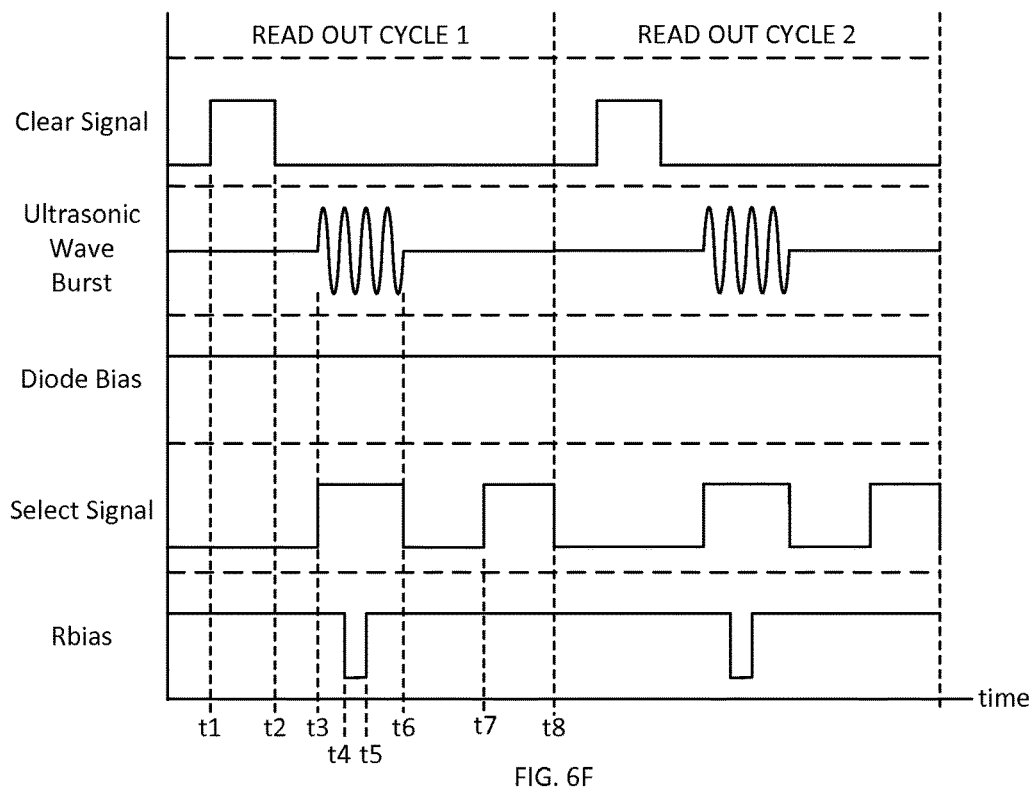
FIG. 6F illustrates a timing diagram associated with still another exemplary operation of the pixel sensor of FIG. 6A in accordance with another aspect of the disclosure.

FIG. 6B illustrates a side cross-sectional view of a portion of the exemplary pixel sensor 600 in accordance with another aspect of the disclosure. As illustrated, the receiving piezoelectric layer 640 is disposed on a pixel receiver that includes the exemplary pixel sensor 600, which, as discussed, is part of an array of pixel sensors of a CMOS receiver formed on an IC substrate (e.g., Silicon (Si) substrate). Also, as illustrated, the pixel sensor 600 comprises the NMOS N1 including a drain (D), gate (G), and source (S). As customary, the gate is formed above the substrate, and specifically, above a channel situated between the drain (D) and source (s), whereby the drain (D), channel, and source (S) are formed within the substrate.

The pixel sensor 600 further comprises a plurality of metallization layers situated above the substrate. In this example, there are three (3) metallization layers M1, M2, and M3, wherein only a relevant portion of metallization layers M1 is shown. It shall be understood that the pixel sensor 600 may be configured with any number of metallization layers. The lowest metallization layer M1 (closest to the substrate) is electrically isolated from the substrate by a first insulating layer I1 (e.g., an oxide). Similarly, the second metallization layer M2 (immediately above the first metallization layer M1) is electrically isolated from the first metallization layer M1 by a second insulating layer I2 (e.g., an oxide). In a like manner, the third metallization layer M3 (immediately above the second metallization layer M2) is electrically isolated from the second metallization layer M2 by a third insulating layer I3 (e.g., an oxide). A passivation layer I4 (e.g., an oxide) may be disposed over the top metallization layer M3 to protect the M3 layer.

The top metallization layer M3 serves as the input metallization pad 610 for the pixel sensor 600. Similar to pixel sensor 500, the area of the top metallization layer M3 is configured relatively large (e.g., approximately 80 percent of the entire pixel region of the pixel sensor). Again, the reason for this is to essentially maximize the sensor capacitance between the top surface of the piezoelectric layer 640 and the top metallization layer M3. The sensor capacitance is essentially maximized to increase the input pixel voltage developed at the top metallization layer M3 in response to an ultrasonic wave reflected off a user's finger.

In this exemplary embodiment, the second metallization layer M2 is configured as the shield to reduce the parasitic capacitance CP between the input metallization pad 610 (e.g., the top metallization layer M3) and the grounded substrate. Similar to pixel sensor 600, the area of the second metallization layer M2 is larger than the area of the top metallization layer M3. For example, the area of the second metallization layer M2 may be 90 percent of the pixel region, whereas the area of the top metallization layer M3 may be 80 percent of the pixel region. Also, similar to pixel sensor 500, the position of the second metallization layer M2 is such that all vertical linear paths between the top metallization layer M3 and the substrate intersect with the second metallization layer M2. This maximizes the shielding properties of the second metallization layer M2.

Also, similar to pixel sensor, the second metallization layer M2 may include a metallized pad and a gap, wherein the metallized pad is electrically coupled to the top metallization layer M3 by way of a metallized via hole V2 and coupled to the gate of NMOS N1 by way of another metallized via hole V1A, a corresponding metallized pad in the first metallization layer M1, and a gate contact. The gap is configured to electrically isolate the metallized pad of the second metallization layer M2 from the shielding portion of the second metallization layer M2. It shall be understood the second metallization layer M2 may include one or more additional pads/gaps to facilitate electrical connections through the shielding portion of the second metallization layer M2, as may be required by the pixel sensor 600.

Referring back to FIG. 6B, the source of NMOS N1 is coupled to the second metallization layer M2 by way of a source contact, the first metallization layer M1, and a metallized via hole V1B between the first and second metallization layers M1 and M2. Accordingly, such electrical connection between the source of NMOS N1 and the second metallization layer M2 ensures that the voltage at the shielding portion of the second metallization layer M2 is substantially the same as the voltage at the top metallization layer M3. This substantially reduces the equivalent parasitic capacitance coupled between the input metallization pad and the grounded substrate. As in pixel sensor 500, the voltage at the second metallization layer M2 need not be substantially the same as the voltage at the top metallization layer M3 for some capacitance cancellation to occur. In such case, the voltage at the second metallization layer M2 should be based on the voltage at the top metallization layer M3.

Also, as illustrated in FIG. 6B, the second parasitic capacitance CP2 between the second metallization layer M2 and the grounded substrate is not significantly coupled to the top metallization layer M3; and hence, does not significantly reduce the input pixel voltage at the top metallization layer M3. Thus, the sensitivity of the pixel sensor 600 is improved by configuring the second metallization layer M2 as a shield through the use of the electrical connection of the source of NMOS N1 to the second metallization layer M2.

FIGS. 6C-6F illustrate timing diagrams associated with exemplary operations of the pixel sensor 600 in accordance with another aspect of the disclosure. The timing diagrams associated with the operations of the pixel sensor 600 are similar to the timing diagrams associated with pixel sensor 400 as depicted in FIGS. 4B-4E, except that the select signal is asserted during a first time interval for capacitance cancellation purposes, and during a second time interval for output voltage readout purposes.

In particular, the select signal is asserted during time interval t3-t6 so that the NMOS N1 is configured as a source-follower amplifier. As such, the source voltage of NMOS N1, which tracks the gate voltage of NMOS N1, is applied to the shielding metallization layer M2 for reducing the parasitic capacitance CP as previously discussed. This time interval t3-t6 coincides with the generation of the ultrasonic wave burst so that the sensitivity of the pixel receiver 600 is increased during this interval for better detection of the input pixel voltage. Between times t6-t7, the select signal may be de-asserted. Then, during time interval t7-t8, the select signal is re-asserted to allow a read out of the output pixel voltage VOUT.

Figure 7:
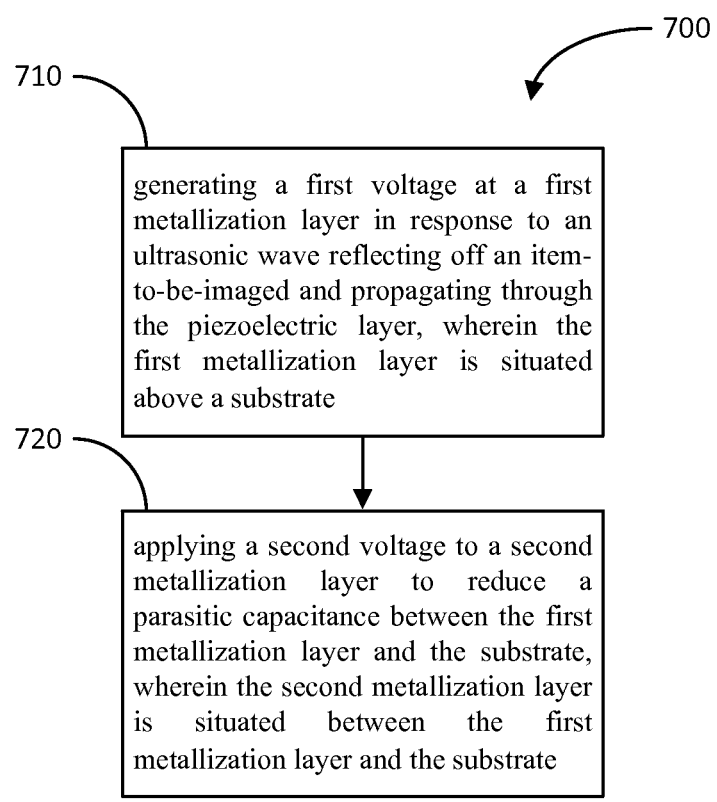
FIG. 7 illustrates a flow diagram of an exemplary method of reducing parasitic capacitance for a pixel sensor in accordance with another aspect of the disclosure.

FIG. 7 illustrates a flow diagram of an exemplary method 700 of reducing parasitic capacitance for a pixel sensor in accordance with another aspect of the disclosure. According to the method 700, a first voltage is generated at a first metallization layer in response to an ultrasonic wave reflecting off an item-to-be-imaged and propagating through the piezoelectric layer, wherein the first metallization layer is situated above a substrate (block 710). Further, according to the method 700, a second voltage is applied to a second metallization layer to reduce a parasitic capacitance between the first metallization layer and the substrate, wherein the second metallization layer is situated between the first metallization layer and the substrate (block 720).

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples described herein but is to be accorded the widest scope consistent with the principles and novel features disclosed herein.

What is claimed is:

1. An apparatus, comprising:
    a first metallization layer coupled to a piezoelectric layer, wherein a first voltage is formed at the first metallization layer in response to an ultrasonic wave reflecting off an item-to-be-imaged and propagating through the piezoelectric layer, and wherein the first metallization layer is situated above a substrate;
    a second metallization layer situated between the first metallization layer and the substrate, wherein the first metallization layer has a first area smaller than a second area of the second metallization layer; and
    a device configured to apply a second voltage to the second metallization layer to reduce a parasitic capacitance between the first metallization layer and the substrate.

2. The apparatus of claim 1, wherein the device is implemented on a CMOS IC comprising the substrate and the first and second metallization layers, and wherein the first and second metallization layers comprise top and second-from-the-top metallization layers of the CMOS IC, respectively.

3. The apparatus of claim 1, wherein the device comprises a buffer amplifier including an input coupled to the first metallization layer and an output coupled to the second metallization layer.

4. The apparatus of claim 1, wherein the device comprises a source-follower amplifier including a field effect transistor (FET) having a gate coupled to the first metallization layer and a source coupled to the second metallization layer.

5. The apparatus of claim 4, wherein the gate of the FET is coupled to the first metallization layer by way of a metallization pad formed in the second metallization layer, wherein the metallization pad is electrically isolated from another portion of the second metallization layer.

6. The apparatus of claim 4, wherein the source of the FET is coupled to the second metallization layer by way of a metallized via hole.

7. The apparatus of claim 4, wherein the source of the FET is coupled to the second metallization layer by way of a metallization pad formed in a third metallization layer, wherein the third metallization layer is situated between the second metallization layer and the substrate.

8. The apparatus of claim 1, wherein the second voltage is substantially the same as the first voltage.

9. The apparatus of claim 1, wherein the second metallization layer is configured such that all vertical linear paths from the first metallization layer to the substrate intersect with the second metallization layer.

10. A method, comprising:
generating a first voltage at a first metallization layer in response to an ultrasonic wave reflecting off an item-to-be-imaged and propagating through the piezoelectric layer, wherein the first metallization layer is situated above a substrate;
generating a second voltage from the first voltage; and
applying the second voltage to a second metallization layer to reduce a parasitic capacitance between the first metallization layer and the substrate, wherein the second metallization layer is situated between the first metallization layer and the substrate, and the first metallization layer has a first area smaller than a second area of the second metallization layer.

11. The method of claim 10, wherein a CMOS IC comprises the substrate and the first and second metallization layers, and wherein the first and second metallization layers comprise top and second-from-the-top metallization layers of the CMOS IC, respectively.

12. The method of claim 10, wherein applying the second voltage to the second metallization layer comprises amplifying the first voltage using a buffer amplifier to generate the second voltage.

13. The method of claim 10, wherein applying the second voltage to the second metallization layer comprises amplifying the first voltage using a source-follower amplifier including a field effect transistor (FET), wherein the FET includes a gate receiving the first voltage and a source generating the second voltage.

14. The method of claim 13, wherein the gate of the FET is coupled to the first metallization layer by way of a metallization pad formed in the second metallization layer, wherein the metallization pad is electrically isolated from another portion of the second metallization layer.

15. The method of claim 13, wherein the source of the FET is coupled to the second metallization layer by way of a metallized via hole.

16. The method of claim 13, wherein the source of the FET is coupled to the second metallization layer by way of a metallization pad formed in a third metallization layer, wherein the third metallization layer is situated between the second metallization layer and the substrate.

17. The method of claim 10, wherein the second voltage is substantially the same as the first voltage.

18. The method of claim 10, wherein the second metallization layer is configured such that all vertical linear paths from the first metallization layer to the substrate intersect with the second metallization layer.

19. An apparatus, comprising:
means for generating a first voltage at a first metallization layer in response to an ultrasonic wave reflecting off an item-to-be-imaged and propagating through the piezoelectric layer, wherein the first metallization layer is situated above a substrate;
and
means for applying a second voltage to a second metallization layer to reduce a parasitic capacitance between the first metallization layer and the substrate, wherein the second metallization layer is situated between the first metallization layer and the substrate, and the first metallization layer has a first area smaller than a second area of the second metallization layer.

20. The apparatus of claim 19, wherein a CMOS IC comprises the substrate and the first and second metallization layers, and wherein the first and second metallization layers comprise top and second-from-the-top metallization layers of the CMOS IC, respectively.

21. The apparatus of claim 19, wherein the means for applying the second voltage to the second metallization layer comprises means for amplifying the first voltage to generate the second voltage.

22. The apparatus of claim 19, wherein the means for applying the second voltage to the second metallization layer comprises means for amplifying the first voltage using source-follower including a field effect transistor (FET), wherein the FET includes a gate receiving the first voltage and a source generating the second voltage.

23. The apparatus of claim 22, wherein the gate of the FET is coupled to the first metallization layer by way of a metallization pad formed in the second metallization layer, wherein the metallization pad is electrically isolated from another portion of the second metallization layer.

24. The apparatus of claim 22, wherein the source of the FET is coupled to the second metallization layer by way of a metallized via hole.

25. The apparatus of claim 22, wherein the source of the FET is coupled to the second metallization layer by way of a metallization pad formed in a third metallization layer, wherein the third metallization layer is situated between the second metallization layer and the substrate.

26. The apparatus of claim 19, wherein the second voltage is substantially the same as the first voltage.

27. The apparatus of claim 19, wherein the second metallization layer is configured such that all vertical linear paths from the first metallization layer to the substrate intersect with the second metallization layer.

* * * * *